(12) United States Patent
Nakamura et al.

(10) Patent No.: US 7,262,035 B2
(45) Date of Patent: Aug. 28, 2007

(54) METHOD FOR PRODUCING L-GLUTAMINE BY FERMENTATION AND L-GLUTAMINE PRODUCING BACTERIUM

(75) Inventors: Jun Nakamura, Kawasaki (JP); Hiroshi Izui, Kawasaki (JP); Kayo Moriguchi, Kawasaki (JP); Hiroki Kawashima, Kawasaki (JP); Tsuyoshi Nakamatsu, Tokyo (JP); Osamu Kurahashi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 240 days.

(21) Appl. No.: 10/062,458

(22) Filed: Feb. 5, 2002

(65) Prior Publication Data

US 2003/0003550 A1   Jan. 2, 2003

(30) Foreign Application Priority Data

Feb. 5, 2001 (JP) ............................. 2001-028163
May 30, 2001 (JP) ............................. 2001-162806

(51) Int. Cl.
C12P 13/14 (2006.01)
C12N 9/00 (2006.01)
C12N 1/20 (2006.01)
C12N 15/00 (2006.01)
C07H 21/04 (2006.01)

(52) U.S. Cl. .................. 435/110; 435/106; 435/183; 435/193; 435/252.33; 435/320.1; 536/23.2

(58) Field of Classification Search ................ 435/183, 435/193, 252.33, 320.1, 106, 110; 536/23.2; 453/69.1, 183, 193, 252.3, 252.33
See application file for complete search history.

(56) References Cited

U.S. PATENT DOCUMENTS 3,886,039 A   5/1975   Yoshinaga et al.

FOREIGN PATENT DOCUMENTS

| CN | 1225946 | 8/1999 |
|---|---|---|
| CN | 1067434 | 6/2001 |
| EP | 0756007 A2 * | 1/1997 |
| WO | WO 01/00843 | 1/2001 |

OTHER PUBLICATIONS

Attwood et al. Which craft is best in bioinformatics? Comput. Chem. 2001, vol. 25(4), pp. 329-339.*
Ponting, C.P. Issues in predicting protein function from sequence. Brief. Bioinform. Mar. 2001, vol. 2(1), pp. 19-29.*
Patent Abstracts of Japan, JP 03-232497, Oct. 16, 1991.
M. Jakoby, et al., FEMS Microbiology Letters, vol. 154, pp. 81-88, "Isolation of the Corynebacterium Glutamicum glnA Gene Encoding Glutamine Synthetase I", 1997.
S. T. Cole, et al., Nature, vol. 393, GenBank Accession No. Z70692, 20 pages, "Deciphering the Biology of Mycobacterium Tuberculosis From the Complete Genome Sequence", 1998.
D. Fink, et al., Microbiology, vol. 145, GenBank Accession No. Y17736, 3 pages, "Nitrogen Metabolism in Streptomyces Coelicolor A3 (2): Modification of Glutamine Synthetase I by an Adenylyltransferase", 1999.
Database EMBL 'Online', AN AX063813, pp. 1-2, XP-002226627, Jan. 24, 2001, Sequence 95 From Patent WO 01/00843.
Database EMBL 'Online', AN AX063817, pp. 1-3, XP-002226628, Jan. 24, 2001, Sequence 99 From Patent WO 01/00843.
Database EMBL 'Online', AN AX063814, 1 page, XP-002226629, Jan. 22, 2001, Sequence 96 From Patent WO 01/00843.
Database EMBL 'Online', AN AX063818, 1 page, XP-002226630, Jan. 22, 2001, Sequence 100 From Patent WO 01/00843.
E. R. Börmann, et al., Molecular Microbiology, vol. 6, No. 3, pp. 317-326, XP-000864663, "Molecular Analysis of the Corynebacterium Glutamicum GDH Gene Encoding Glutamate Dehydrogenase", 1992.
M. Jakoby, et al., FEMS Microbiology Letters, vol. 173, pp. 303-310, XP-002226626, "Nitrogen Regulation in Corynebacterium Glutamicum; Isolation of Genes Involved and Biochemical Characterization of Corresponding Proteins", 1999.
Agrobiology Technology Journal, vol. 3, No. 1, 1995, pp. 28-33 (with partial English translation).

* cited by examiner

Primary Examiner—Tekchand Saidha
Assistant Examiner—Christian L. Fronda
(74) Attorney, Agent, or Firm—Oblon, Spivak, McClelland, Maier & Neustadt, P.C.

(57) ABSTRACT

L-Glutamine is produced by culturing a coryneform bacterium which has L-glutamine producing ability and has been modified so that its intracellular glutamine synthetase activity should be enhanced, preferably which has been further modified so that its intracellular glutamate dehydrogenase activity should be enhanced, in a medium to produce and accumulate L-glutamine in the medium and collecting the L-glutamine.

10 Claims, No Drawings

METHOD FOR PRODUCING L-GLUTAMINE BY FERMENTATION AND L-GLUTAMINE PRODUCING BACTERIUM

BACKGROUND OF THE INVENTION

1. Field of the Invention

The present invention relates to an L-glutamine producing bacterium belonging to coryneform bacteria and a method for producing L-glutamine. L-Glutamine is an industrially useful amino acid as an ingredient of seasonings, liver function promoting agents, amino acid transfusions, comprehensive amino acid preparations and so forth.

2. Related Art

In order to produce L-amino acids by fermentation, methods for improving microorganisms by breeding have been used abundantly. That is, since production ability of wild strains per se for L-amino acid production is extremely low in many cases, there have been known methods of imparting auxotrophy or analogue resistance by mutation or imparting mutation for metabolic regulation and methods utilizing a combination of these. Although L-glutamine can be obtained with an appropriate yield by the aforementioned methods, it is indispensable to further improve the fermentation yield in order to industrially produce L-glutamine at a low cost.

Further, the L-glutamine fermentation also suffers from the problem of by-production of L-glutamic acid. A method for solving this problem is proposed in, for example, Japanese Patent Laid-open Publication (Kokai) No. 3-232497. Although the production of L-glutamic acid can be suppressed to a certain extent by this method, there is still by-production of L-glutamic acid and the yield of L-glutamine is insufficient.

Since such improvements of L-glutamine producing bacteria as mentioned above utilize methods of treating a host bacterium with a mutagenizing agent or the like and selecting a strain showing improved productivity for L-glutamine from bacteria randomly incorporated with mutations, they require much labor and suffer from difficulties.

SUMMARY OF THE INVENTION

An object of the present invention is to find characteristics of coryneform bacteria providing improvement of L-glutamine productivity and suppression of by-production of L-glutamic acid, and thereby provide a method for producing L-glutamine utilizing a strain having such characteristics.

The inventors of the present invention assiduously studied in order to achieve the aforementioned object. As a result, they found that a strain of coryneform bacterium of which intracellular glutamine synthetase activity was enhanced showed more excellent L-glutamine producing ability and could markedly suppress the by-production of L-glutamic acid compared with strains showing the glutamine synthetase activity comparable to that of wild strains. Further, they found that production rate of L-glutamine was improved by simultaneously enhancing glutamine synthetase activity and glutamate dehydrogenase activity. Furthermore, they successfully isolated a novel gene coding for glutamine synthetase and a novel gene coding for glutamine synthetase adenylyl transferase, and thus accomplished the present invention.

That is, the present invention provides the followings.

(1) A coryneform bacterium which has L-glutamine producing ability and has been modified so that its intracellular glutamine synthetase activity should be enhanced.

(2) The bacterium according to (1), wherein the glutamine synthetase activity is enhanced by increasing expression amount of a glutamine synthetase gene.

(3) The bacterium according to (2), wherein the expression amount of the glutamine synthetase gene is increased by increasing copy number of a gene coding for glutamine synthetase or modifying an expression control sequence of the gene so that expression of the gene coding for the intracellular glutamine synthetase of the bacterium should be enhanced.

(4) The bacterium according to (1), wherein the glutamine synthetase activity is enhanced by deficiency in activity control of intracellular glutamine synthetase by adenylylation.

(5) The bacterium according to (4), wherein the activity control of intracellular glutamine synthetase by adenylylation is defected by one or more of harboring glutamine synthetase of which activity control by adenylylation is defected, decrease of glutaimine synthetase adenylyl transferase activities in the bacterial cell and decrease of PII protein activity in the bacterial cell.

(6) The bacterium according to any one of (1) to (5), wherein the bacterium has been further modified so that its intracellular glutamate dehydrogenase activity should be enhanced.

(7) The bacterium according to (6), wherein the glutamate dehydrogenase activity is enhanced by increasing expression amount of a glutamate dehydrogenase gene.

(8) The bacterium according to (7), wherein the expression amount of the glutamate dehydrogenase gene is increased by increasing copy number of the gene coding for glutamate dehydrogenase or modifying an expression control sequence of the gene so that expression of the gene coding for the intracellular glutamate dehydrogenase of the bacterium should be increased.

(9) A method for producing L-glutamine, which comprises culturing a bacterium according to any one of (1) to (8) in a medium to produce and accumulate L-glutamine in the medium and collecting the L-glutamine.

(10) A DNA coding for a protein defined in the following (A) or (B):

(A) a protein that has the amino acid sequence of SEQ ID NO: 2, (B) a protein that has the amino acid sequence of SEQ ID NO: 2 including substitution, deletion, insertion, addition or inversion of one or several amino acid residues and has glutamine synthetase activity.

(11) The DNA according to (10), which is a DNA defined in the following (a) or (b):

(a) a DNA containing the nucleotide sequence of the nucleotide numbers 659–1996 in the nucleotide sequence of SEQ ID NO: 1, (b) a DNA that is hybridizable with the nucleotide sequence of the nucleotide numbers 659–1996 in the nucleotide sequence of SEQ ID NO: 1 or a probe that can be prepared from the sequence under the stringent conditions and codes for a protein having glutamine synthetase activity.

(12) A DNA coding for a protein defined in the following (C) or (D):

(C) a protein that has the amino acid sequence of SEQ ID NO: 3, (D) a protein that has the amino acid sequence of SEQ ID NO: 3 including substitution, deletion, insertion, addition or inversion of one or several amino acid residues and has glutamine synthetase adenylyl transferase activities.

(13) The DNA according to (12), which is a DNA defined in the following (c) or (d):

(c) a DNA containing the nucleotide sequence of nucleotide numbers 2066–5200 in the nucleotide sequence of SEQ ID NO: 1, (d) a DNA that is hybridizable with the nucleotide sequence of the nucleotide numbers 2006–5200 in the nucleotide sequence of SEQ ID NO: 1 or a probe that can be prepared from the sequence under the stringent conditions and codes for a protein having glutamine synthetase adenylyl transferase activities.

According to the present invention, the by-production of L-glutamic acid can be suppressed and the production efficiency of L-glutamine can be improved in the production of L-glutamine by fermentation utilizing coryneform bacteria. Further, the DNA of the present invention can be used for breeding of L-glutamine producing coryneform bacteria.

PREFERRED EMBODIMENTS OF THE INVENTION

Hereafter, the present invention will be explained in detail.

(1) Coryneform Bacteria of the Present Invention

In the present invention, "coryneform bacteria" include those having hitherto been classified into the genus *Brevibacterium*, but united into the genus *Corynebacterium* at present (*Int. J. Syst. Bacteriol.*, 41, 255 (1981)), and include bacteria belonging to the genus *Brevibacterium* closely relative to the genus *Corynebacterium*. Examples of such coryneform bacteria are mentioned below.

*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium*
*Corynebacterium melassecola*
*Corynebacterium thermoaminogenes*
*Corynebacterium herculis*
*Brevibacterium divaricatum*
*Brevibacterium flavum*
*Brevibacterium immariophilum*
*Brevibacterium lactofermentum*
*Brevibacterium roseum*
*Brevibacterium saccharolyticum*
*Brevibacterium thiogenitalis*
*Brevibacterium ammoniagenes*
*Brevibacterium album*
*Brevibacterium cerium*
*Microbacterium ammoniaphilum*

Specifically, the following strains can be exemplified.
*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium glutamicum* ATCC 13020, 13032, 13060
*Corynebacterium lilium* ATCC 15990
*Corynebacterium melassecola* ATCC 17965
*Corynebacterium thermoaminogenes* AJ12340 (FERM BP-1539)
*Corynebacterium herculis* ATCC 13868
*Brevibacterium divaricatum* ATCC 14020
*Brevibacterium flavum* ATCC 13826, ATCC 14067, AJ12418 (FERM BP-2205)
*Brevibacterium immariophilum* ATCC 14068
*Brevibacterium lactofermentum* ATCC 13869
*Brevibacterium roseum* ATCC 13825
*Brevibacterium saccharolyticum* ATCC 14066
*Brevibacterium thiogenitalis* ATCC 19240
*Brevibacterium ammoniagenes* ATCC 6871, ATCC 6872
*Brevibacterium album* ATCC 15111
*Brevibacterium cerium* ATCC 15112
*Microbacterium ammoniaphilum* ATCC 15354

To obtain these strains, one can be provided them from, for example, the American Type Culture Collection (10801 University Boulevard, Manassas, Va. 20110-2209, United States of America). That is, each strain is assigned its registration number, and one can request provision of each strain by utilizing its registration number. The registration numbers corresponding to the strains are indicated on the catalog of the American Type Culture Collection. Further, the AJ12340 strain was deposited on Oct. 27, 1987 at the National Institute of Bioscience and Human-Technology, Agency of Industrial Science and Technology, Ministry of International Trade and Industry (currently, the independent administrative corporation, National Institute of Advanced Industrial Science and Technology, International Patent Organism Depositary (Chuo Dai-6, 1-1 Higashi 1-Chome, Tsukuba-shi, Ibaraki-ken, Japan, postal code: 305-8566)) as an international deposit under the provisions of the Budapest Treaty, and received an accession number of FERM BP-1539. The AJ12418 strain was deposited on Jan. 5, 1989 at the National Institute of Bioscience and Human-Technology, Agency of Industrial Science and Technology, Ministry of International Trade and Industry as an international deposit under the provisions of the Budapest Treaty and received an accession number of FERM BP-2205.

In the present invention, "L-glutamine producing ability" means an ability to accumulate L-glutamine in a medium, when the coryneform bacterium of the present invention is cultured in the medium. This L-glutamine producing ability may be possessed by the bacterium as a property of a wild strain of coryneform bacteria or may be imparted or enhanced by breeding.

For imparting or enhancing the L-glutamine producing ability by breeding, there can be used the method of isolation of 6-diazo-5-oxo-norleucine resistant strain (Japanese Patent Laid-open Publication No. 3-232497), the method of isolation of purine analogue resistant and/or methionine sulfoxide resistant strain (Japanese Patent Laid-open Publication No. 61-202694), the method of isolation of α-ketomalonic acid resistant strain (Japanese Patent Laid-open Publication No. 56-151495), the method of imparting resistance to a peptide containing glutamic acid (Japanese Patent Laid-open Publication No. 2-186994) and so forth. As specific examples of coryneform bacteria having L-glutamine producing ability, the following strains can be mentioned.

*Brevibacterium flavum* AJ11573 (FERM P-5492, refer to Japanese Patent Laid-open Publication No. 56-151495)
*Brevibacterium flavum* AJ12210 (FERM P-8123, refer to Japanese Patent Laid-open Publication No. 61-202694)
*Brevibacterium flavum* AJ12212 (FERM P-8123, refer to Japanese Patent Laid-open Publication No. 61-202694)
*Brevibacterium flavum* AJ12418 (FERM-BP2205, refer to Japanese Patent Laid-open Publication No. 2-186994)
*Brevibacterium flavum* DH18 (FERM P-11116, refer to Japanese Patent Laid-open Publication No. 3-232497)
*Corynebacterium melassecola* DH344 (FERM P-11117, refer to Japanese Patent Laid-open Publication No. 3-232497)

Corynebacterium glutamicum AJ11574 (FERM P-5493, refer to Japanese Patent Laid-open Publication No. No. 56-151495)

The term "modified so that intracellular glutamine synthetase (henceforth also referred to as "GS") activity should be enhanced" means that the GS activity per cell has become higher than that of a non-modified strain, for example, a wild-type coryneform bacterium. For example, there can be mentioned a case where number of GS molecules per cell increases, a case where GS specific activity per GS molecule increases and so forth. Further, as a wild-type coryneform bacterium that serves as an object for comparison, for example, the *Brevibacterium flavum* ATCC 14067 can be mentioned. As a result of enhancement of intracellular GS activity, there are obtained an effect that the amount of L-glutamine accumulation in a medium increases, an effect that the by-production of L-glutamic acid decreases and so forth.

Enhancement of GS activity in a coryneform bacterium cell can be attained by enhancement of expression of a gene coding for GS. Increase of the expression amount of the gene can be attained by increasing copy number of the gene coding for GS. For example, a recombinant DNA can be prepared by ligating a gene fragment coding for GS with a vector functioning in the bacterium, preferably a multi-copy type vector, and introduced into a host having L-glutamine producing ability to transform it. Alternatively, the aforementioned recombinant DNA can be introduced into a wild-type coryneform bacterium to obtain a transformant, and then the transformant can be imparted with L-glutamine producing ability.

As the GS gene, any of genes derived from coryneform bacteria and genes derived from other organisms such as bacteria belonging to the genus *Escherichia* can be used. Among these, genes derived from coryneform bacteria are preferred in view of ease of expression.

As the gene coding for GS of coryneform bacteria, glnA has already been elucidated (*FEMS Microbiology Letters*, 81–88, 154, 1997). Therefore, a GS gene can be obtained by PCR (polymerase chain reaction; refer to White, T. J. et al., *Trends Genet.*, 5, 185 (1989)) utilizing primers prepared based on the nucleotide sequence of the gene, for example, the primers mentioned in Sequence Listing as SEQ ID NOS: 4 and 5, and chromosomal DNA of coryneform bacterium as a template. Genes coding for GS of other microorganisms can be obtained in a similar manner.

The chromosomal DNA can be prepared from a bacterium, which is a DNA donor, by the method of Saito and Miura (refer to H. Saito and K. Miura, *Biochem. Biophys. Acta*, 72, 619 (1963), Text for Bioengineering Experiments, Edited by the Society for Bioscience and Bioengineering, Japan, pp.97–98, Baifukan, 1992), for example.

Incidentally, an isozyme often exists for an enzyme involved in an amino acid biosynthesis system. The inventors of the present invention successfully isolated and cloned a gene coding for an isozyme of GS of coryneform bacteria by utilizing homology with respect to the nucleotide sequence of the aforementioned glnA gene. This gene is referred to as "glnA2". The process for obtaining it will be described later. glnA2 as well as glnA can be used for enhancement of the GS activity of coryneform bacteria.

If the GS gene amplified by the PCR method is ligated to a vector DNA autonomously replicable in a cell of *Escherichia coli* and/or coryneform bacteria to prepare a recombinant DNA and this is introduced into *Escherichia coli*, subsequent procedures become easy. Examples of the vector autonomously replicable in a cell of *Escherichia coil* include pUC19, pUC18, pHSG299, pHSG399, pHSG398, RSF1010, pBR322, pACYC184, pMW219 and so forth.

A vector that functions in coryneform bacteria means, for example, a plasmid that can autonomously replicate in coryneform bacteria. Specific examples thereof include the followings.

pAM330 (refer to Japanese Patent Laid-open Publication No. 58-67699)
pHM1519 (refer to Japanese Patent Laid-open Publication No. 58-77895)

Moreover, if a DNA fragment having an ability to make a plasmid autonomously replicable in coryneform bacteria is taken out from these vectors and inserted into the aforementioned vectors for *Escherichia coli*, they can be used as a so-called shuttle vector autonomously replicable in both of *Escherichia coli* and coryneform bacteria.

Examples of such a shuttle vector include those mentioned below. There are also indicated microorganisms that harbor each vector, and accession numbers thereof at the international depositories are shown in the parentheses, respectively.

pAJ655 *Escherichia coli* AJ11882 (FERM BP-136) *Corynebacterium glutamicum* SR8201 (ATCC 39135)
pAJ1844 *Escherichia coli* AJ11883 (FERM BP-137) *Corynebacterium glutamicum* SR8202 (ATCC 39136)
pAJ611 *Escherichia coli* AJ11884 (FERM BP-138)
pAJ3148 *Corynebacterium glutamicum* SR8203 (ATCC 39137)
pAJ440 *Bacillus subtilis* AJ11901 (FERM BP-140)
pHC4 *Escherichia coli* AJ12617 (FERM BP-3532)

These vectors can be obtained from the deposited microorganisms as follows. That is, microbial cells collected in their exponential growth phase are lysed by using lysozyme and SDS, and centrifuged at 30000×g. The supernatant obtained from the lysate is added with polyethylene glycol, fractionated and purified by cesium chloride-ethidium bromide equilibrium density gradient centrifugation.

In order to prepare a recombinant DNA by ligating a GS gene and a vector that can function in a cell of coryneform bacterium, a vector is digested with a restriction enzyme corresponding to the terminus of the gene containing the GS gene. Ligation is usually performed by using a ligase such as T4 DNA ligase.

To introduce the recombinant DNA prepared as described above into a microorganism, any known transformation methods that have hitherto been reported can be employed. For instance, employable are a method of treating recipient cells with calcium chloride so as to increase the permeability of DNA, which has been reported for *Escherichia coli* K-12 (Mandel, M. and Higa, A., *J. Mol. Biol.*, 53, 159 (1970)), and a method of preparing competent cells from cells which are at the growth phase followed by introducing the DNA thereinto, which has been reported for *Bacillus subtilis* (Duncan, C. H., Wilson, G. A. and Young, F. E., *Gene*, 1, 153 (1977)). In addition to these, also employable is a method of making DNA-recipient cells into protoplasts or spheroplasts, which can easily take up recombinant DNA, followed by introducing the recombinant DNA into the cells, which is known to be applicable to *Bacillus subtilis*, actinomycetes and yeasts (Chang, S. and Choen, S. N., *Molec. Gen. Genet.*, 168, 111 (1979); Bibb, M. J., Ward, J. M. and Hopwood, O. A., *Nature*, 274, 398 (1978); Hinnen, A., Hicks, J. B. and Fink, G. R., *Proc. Natl. Sci. USA*, 75, 1929 (1978)). The transformation of coryneform bacteria can also be performed by the electric pulse method (Sugimoto et al., Japanese Patent Laid-open No. 2-207791).

Increase of copy number of GS gene can also be achieved by introducing multiple copies of the GS gene into chromosomal DNA of coryneform bacteria. In order to introduce multiple copies of the GS gene into chromosomal DNA of coryneform bacteria, homologous recombination is carried out by using a sequence whose multiple copies exist in the chromosomal DNA as targets. As sequences whose multiple copies exist in the chromosomal DNA, repetitive DNA, inverted repeats existing at the end of a transposable element can be used. Also, as disclosed in Japanese Patent Laid-open No. 2-109985, it is possible to incorporate the GS gene into transposon, and allow it to be transferred to introduce multiple copies of the gene into the chromosomal DNA.

Enhancement of the GS activity can also be attained by, besides being based on the aforementioned gene amplification, replacing an expression control sequence of the GS gene on chromosomal DNA or plasmid, such as a promoter, with a stronger one. For example, lac promoter, trp promoter, trc promoter and so forth are known as strong promoters. Moreover, it is also possible to introduce nucleotide substitution for several nucleotides into a promoter region for the GS gene so that it should be modified into a stronger one, as disclosed in International Patent Publication WO00/18935. By such substitution or modification of promoter, expression of the GS gene is enhanced and thus GS activity is enhanced. Such modification of expression control sequence may be combined with the increase of copy number of the GS gene.

The substitution of expression control sequence can be performed, for example, in the same manner as the gene substitution using a temperature sensitive plasmid described later. Examples of the temperature sensitive plasmid of coryneform bacteria include p48K, pSFKT2 (refer to Japanese Patent Laid-open Publication No. 2000-262288 for the both), pHSC4 (refer to France Patent Laid-open Publication No. 2667875, 1992 and Japanese Patent Laid-open Publication No. 5-7491) and so forth. These plasmids can at least autonomously replicate at a temperature of 25° C., but cannot autonomously replicate at a temperature of 37° C. in coryneform bacteria. Although pSFKT2 was used for the substitution for the promoter sequence of the GDH gene in the example mentioned later, gene substitution can be performed in a similar manner by using pHSC4 instead of pSFKT2. *Escherichia coli* AJ12571 harboring pHSC4 was deposited on Oct. 11, 1990 at the National Institute of Bioscience and Human-Technology, Agency of Industrial Science and Technology, Ministry of International Trade and Industry (currently, the independent administrative corporation, National Institute of Advanced Industrial Science and Technology, International Patent Organism Depositary (Chuo Dai-6, 1-1 Higashi 1-Chome, Tsukuba-shi, Ibaraki-ken, Japan, postal code: 305-8566)), and received an accession number of FERM P-11763. Then, it was transferred to an international deposit under the provisions of the Budapest Treaty on Aug. 26, 1991, and received an accession number of FERM BP-3524.

Enhancement of the GS activity can be attained also by deficiency in regulation by the adenylylation of intracellular GS, besides based on the increase of expression amount of the GS gene described above. GS changes into an inactive form by adenylylation of a tyrosine residue in the amino acid sequence (*Proc. Natl. Acad. Sci. USA*, 642–649, (58) 1967; *J. Biol. Chem.*, 3769–3771, (243) 1968). Therefore, by defect of this adenylylation of GS, the intracellular GS activity can be enhanced. The defect of adenylylation used herein means not only substantially complete deregulation by the adenylylation but also such reduction of the adenylylation that the intracellular GS activity should be enhanced.

The adenylylation of GS is generally performed by adenylyl transferase (*Proc. Natl. Acad. Sci. USA*, 1703–1710, (58) 1967). It has been suggested that, in coryneform bacteria, the 405th tyrosine residue of the glnA gene product, which is represented by the sequence of Genebank accession Y13221, (SEQ ID NO: 25), is adenylylated (FEMS Microbiology Letters, 303–310, 1999 (173)). This inactivation by the adenylylation of GS can be canceled by introducing a mutation into the glnA gene so that the tyrosine residue should be replaced with another amino acid residue.

Further, the inactivation of GS by the adenylylation can also be defected by reducing the activities of intracellular glutamine synthetase adenylyl transferase (ATase). Although adenylyl transferase of coryneform bacteria had been unknown, the inventors of the present invention successfully isolated a gene coding for adenylyl transferase of coryneform bacteria, glnE. The process therefor will be described later.

To reduce the intracellular ATase activity of coryneform bacteria, there can be used, for example, a method of treating the coryneform bacteria by ultraviolet irradiation or with a mutagenizing agent used for usual mutagenesis treatment such as N-methyl-N'-nitro-N-nitrosoguanidine (NTG) or a nitrous acid and selecting a mutant strain in which the ATase activity is reduced. Coryneform bacteria having reduced ATase activity can also be obtained by gene disruption, besides the mutagenesis treatment. That is, a coryneform bacterium can be transformed with a DNA containing a glnE gene modified with deletion of partial sequence of the gene coding for ATase so as not to produce ATase functioning normally (deletion type glnE gene), so that recombination between the deletion type glnE gene and the glnE gene on the chromosome should occur to disrupt the glnE gene on the chromosome. Such gene disruption by gene substitution utilizing homologous recombination has already been established, and there are methods utilizing a linear DNA, a plasmid that contains a temperature sensitive replication origin and so forth.

A glnE gene on host chromosome can be replaced with the deletion type glnE gene, for example, as follows. That is, a recombinant DNA is prepared by inserting a temperature sensitive replication origin, a mutant glnE gene and a marker gene for resistance to a drug such as chloramphenicol, and a coryneform bacterium is transformed with the recombinant DNA. Further, the transformant is cultured at a temperature at which the temperature sensitive replication origin does not function, and then the transformant strain can be cultured in a medium containing the drug to obtain a transformant strain in which the recombinant DNA is incorporated into the chromosomal DNA.

In such a strain in which recombinant DNA is incorporated into chromosomal DNA as described above, the mutant glnE gene is recombined with the glnE gene originally present on the chromosome, and the two fusion genes of the chromosomal glnE gene and the deletion type glnE gene are inserted into the chromosome so that the other portions of the recombinant DNA (vector segment, temperature sensitive replication origin and drug resistance marker) should be present between the two fusion genes. Therefore, the transformant strain expresses normal ATase, because the normal glnE gene is dominant in this state.

Then, in order to leave only the deletion type glnE gene on the chromosomal DNA, one copy of the glnE gene is eliminated together with the vector segment (including the temperature sensitive replication origin and the drug resistance marker) from the chromosomal DNA by recombination of two of the glnE genes. In this case, the normal glne gene is left on the chromosomal DNA, and the deletion type glnE gene is excised from the chromosomal DNA, or to the contrary, the deletion type glnE gene is left on the chromosomal DNA, and the normal glnE gene is excised from the chromosome DNA. In the both cases, the excised DNA may be retained in the cell as a plasmid when the cell is cultured at a temperature at which the temperature sensitive replication origin can function. Subsequently, if the cell is cultured at a temperature at which the temperature sensitive replication origin cannot function, the glnE gene on the plasmid is eliminated together with the plasmid from the cell. Then, a strain in which glnE gene is disrupted can be obtained by selecting a strain in which the deletion type glnE gene is left on the chromosome using PCR, Southern hybridization or the like.

Further, the inactivation of GS by the adenylylation can also be canceled by reducing the intracellular activity of PII protein. It is known that the PII protein is also involved in the adenylylation of GS by ATase. The PII protein is a signal transfer protein for controlling the GS activity, and it is known to be uridylylated by uridylyl transferase (UTase). The uridylylated PII protein promotes deadenylylation of GS by ATase, and the deuridylylated PII protein promotes the adenylylation of GS by ATase.

It is reported that GS is highly adenylylated in a UTase deficient strain (*J. Bacteriology*, 569–577, (134) 1978). This phenotype of excessive adenylylation is suppressed by mutation of the PII protein (*J. Bacteriology*, 816–822, (164) 1985). That is, the inactivation of GS by the adenylylation can also be defected by reduction of PII protein activity. The reduction of PII protein activity means reduction of the function for promoting the adenylylation by ATase. The glnB gene coding for the PII protein of coryneform bacteria has been already isolated, and it is suggested that the suppression of GS by the adenylylation of GS is defected by deletion of the gene (*FEMS Microbiology Letters*, 303–310, (173) 1999).

To reduce the PII protein activity of coryneform bacteria, there can be used, for example, a method of treating the coryneform bacteria by ultraviolet irradiation or with a mutagenizing agent used for usual mutagenesis treatment such as N-methyl-N'-nitro-N-nitrosoguanidine (NTG) or a nitrous acid and selecting a mutant strain in which the activity of PII protein is reduced. Coryneform bacteria having reduced PII protein activity can also be obtained by gene disruption, besides the mutagenesis treatment. That is, a coryneform bacterium can be transformed with DNA containing a glnB gene modified with deletion of partial sequence of the gene coding for PII protein so as not to produce PII protein functioning normally (deletion type glnB gene), so that recombination between the deletion type glnB gene and the glnB gene on the chromosome should occur to disrupt the glnB gene on the chromosome. Such gene destruction by utilizing homologous recombination has already been established, and there are methods utilizing a linear DNA, a plasmid that contains a temperature sensitive replication origin and so forth.

A glnB gene on host chromosome can be replaced with the deletion type glnB gene, for example, as follows. That is, a recombinant DNA is prepared by inserting a temperature sensitive replication origin, a mutant glnB gene and a marker gene for resistance to a drug such as chloramphenicol, and a coryneform bacterium is transformed with the recombinant DNA. Further, the resultant transformant strain is cultured at a temperature at which the temperature sensitive replication origin does not function, and then the transformant strain can be cultured in a medium containing the drug to obtain a transformant strain in which the recombinant DNA is incorporated into the chromosomal DNA.

In such a strain in which recombinant DNA is incorporated into chromosomal DNA as described above, the mutant glnB gene is recombined with the glnB gene originally present on the chromosome, and the two fusion genes of the chromosomal glnB gene and the deletion type glnB gene are inserted into the chromosome so that the other portions of the recombinant DNA (vector segment, temperature sensitive replication origin and drug resistance marker) should be present between the two fusion genes. Therefore, the transformant expresses normal PII protein, because the normal glnB gene is dominant in this state.

Then, in order to leave only the deletion type glnB gene on the chromosomal DNA, one copy of the glnB gene is eliminated together with the vector segment (including the temperature sensitive replication origin and the drug resistance marker) from the chromosomal DNA by recombination of two of the glnB genes. In this case, the normal glnB gene is left on the chromosomal DNA, and the deletion type glnB gene is excised from the chromosomal DNA, or to the contrary, the deletion type glnB gene is left on the chromosomal DNA, and the normal glnB gene is excised from the chromosome DNA. In the both cases, the excised DNA may be stably retained in the cell as a plasmid when the cell is cultured at a temperature at which the temperature sensitive replication origin can function. Subsequently, if the cell is cultured at a temperature at which the temperature sensitive replication origin does not function, the glnB gene on the plasmid is eliminated together with the plasmid from the cell. Then, a strain in which glnB gene is disrupted can be obtained by selecting a strain in which the deletion type glnB gene is left on the chromosome using PCR, Southern hybridization or the like.

Elimination of the adenylylation of GS can also be attained by a combination of two or three items of such mutation of GS that should eliminate the aforementioned adenylylation, reduction of the ATase activity and reduction of the PII protein activity.

Although enhancement of the GS activity can also be realized by elimination of the adenylylation of GS by ATase, it may also be attained by a combination of it with the aforementioned means for increasing copy number of the GS gene or means for modifying an expression control sequence.

In order to efficiently produce L-glutamine by using the coryneform bacterium of the present invention, it is preferable to use a strain that has enhanced glutamate dehydrogenase (henceforth also referred to as "GDH") activity concurrently with the enhanced GS activity.

The term "modified so that intracellular GDH activity should be enhanced" means that the GDH activity per cell has become higher than that of a non-modified strain, for example, a wild-type coryneform bacterium. For example, there can be mentioned a case where number of GDH molecules per cell increases, a case where GDH specific activity per GDH molecule increases and so forth. Further, as a wild-type coryneform bacterium that serves as an object for comparison, for example, the *Brevibacterium flavum* ATCC 14067 can be mentioned. As a result of enhancement of intracellular GDH activity, there are obtained an effect that culture time of a coryneform bacterium having L-glutamine producing ability is shortened.

Enhancement of the GDH activity in a coryneform bacterium cell can be attained by enhancement of expression of a gene coding for GDH. Enhancement of the expression amount of the gene can be attained by increasing copy number of the gene coding for GDH. For example, a recombinant DNA can be prepared by ligating a gene fragment coding for GDH with a vector functioning in the bacterium, preferably a multi-copy type vector, and introduced into a host having L-glutamine producing ability to transform it. Alternatively, the aforementioned recombinant DNA can be introduced into a wild-type coryneform bacterium to obtain a transformant strain, and then the obtained transformant strain can be imparted with L-glutamine producing ability.

As the gene coding for GDH, any of genes derived from coryneform bacteria and genes derived from other organisms such as bacteria belonging to the genus Escherichia can be used. Among these, genes derived from coryneform bacteria are preferred in view of ease of expression.

Nucleotide sequence of a gene coding for GDH (gdh gene) of coryneform bacteria has already been elucidated (*Molecular Microbiology*, 6 (3), 317–326 (1992)). Therefore, a GDH gene can be obtained by PCR utilizing primers prepared based on the nucleotide sequence, for example, the primers mentioned in Sequence Listing as SEQ ID NOS: 12 and 13, and chromosomal DNA of coryneform bacterium as a template. Genes coding for GDH of microorganisms other than coryneform bacteria can also be obtained in a similar manner.

The gdh gene can be introduced into coryneform bacteria in a manner similar to that used for the aforementioned GS gene.

In the coryneform bacterium of the present invention, activities of enzymes other than GS and GDH catalyzing reactions of the L-glutamine biosynthesis may be enhanced. Examples of the enzymes catalyzing reactions of the L-glutamine biosynthesis include isocitrate dehydrogenase, aconitate hydratase, citrate synthase, pyruvate dehydrogenase, phosphoenolpyruvate carboxylase, pyruvate carboxylase, pyruvate kinase, phosphofructokinase and so forth.

Further, activities of enzymes that catalyze reactions branching off from the L-glutamine biosynthesis pathway and producing compounds other than L-glutamine may be reduced or eliminated. Examples of the enzymes catalyzing such reactions include isocitrate lyase, α-ketoglutarate dehydrogenase, glutamate synthase and so forth.

(2) Production of L-glutamine Using Microorganism of the Present Invention

By culturing a coryneform bacterium obtained as described above in a medium to produce and accumulate L-glutamine in the medium and correcting the L-glutamine from the medium, L-glutamine can be efficiently produced and the by-production of L-glutamic acid can be suppressed.

In order to produce L-glutamine by using the coryneform bacterium of the present invention, culture can be performed in a conventional manner using a usual medium containing a carbon source, nitrogen source and mineral salts as well as organic trace nutrients such as amino acids and vitamins, as required. Either a synthetic medium or a natural medium may be used. Any kinds of carbon source and nitrogen source may be used so long as they can be utilized by a strain to be cultured.

As the carbon source, there are used sugars such as glucose, glycerol, fructose, sucrose, maltose, mannose, galactose, starch hydrolysate and molasses, and organic acids such as acetic acid and citric acid, and alcohols such as ethanol can also be used each alone or in a combination with other carbon sources.

As the nitrogen source, there are used ammonia, ammonium salts such as ammonium sulfate, ammonium carbonate, ammonium chloride, ammonium phosphate and ammonium acetate, nitrate salts and so forth.

As the organic trace nutrients, amino acids, vitamins, fatty acids, nucleic acids, those containing those substances such as peptone, casamino acid, yeast extract and soybean protein decomposition product and so forth are used. When an auxotrophic mutant that requires an amino acid or the like for its growth is used, it is preferable to supplement the required nutrient.

As the mineral salts, phosphates, magnesium salts, calcium salts, iron salts, manganese salts and so forth are used.

The culture is performed as aeration culture, while the fermentation temperature is controlled to be 20–45° C., and pH to be 5–9. When pH falls during the culture, the medium is neutralized by addition of calcium carbonate or with an alkali such as ammonia gas. A substantial amount of L-glutamine is accumulated in the culture broth after 10 hours to 120 hours of culture in such a manner as described above.

Collection of L-glutamine from the culture broth after the culture may be performed in a conventional manner. For example, after the cells were removed from the culture broth, L-glutamine can be collected by concentrating the broth to crystallize L-glutamine.

(3) DNA Coding for Protein Having Glutamine Synthetase Activity (glnA2 Gene) and DNA Coding for Protein Having Glutamine Synthetase and Adenylyl Transferase Activities (glnE Gene) According to the Present Invention The first DNA of the present invention is a gene coding for GS. The second DNA of the present invention is a gene coding for ATase. These genes can be obtained from a chromosome DNA library of *Brevibacterium lactofermentum* by hybridization using a partial fragment of a known glnA gene as a probe. The partial fragment of a known glnA gene can be obtained by PCR amplification using chromosome DNA of *Brevibacterium lactofermentum*, for example, *Brevibacterium lactofermentum* ATCC 13869 strain, as a template and the primers shown as SEQ ID NOS: 18 and 19.

Methods of production of genomic DNA library, hybridization, PCR, preparation of plasmid DNA, digestion and ligation of DNA, transformation and so forth for obtaining the DNA of the present invention and enhancement of the GS activity and GDH activity are described in Sambrook, J., Fritsh, E. F. and Maniatis, T., "Molecular Cloning", Cold Spring Harbor Laboratory Press, 1.21, 1989.

The nucleotide sequences of the aforementioned primers were designed based on the nucleotide sequence of a glnA gene of *Corynebacterium glutamicum* (GenBank accession Y13221). By using these primers, a DNA fragment containing a region corresponding to the nucleotide numbers 1921–2282 of the glnA gene (GenBank accession Y13221) can be obtained.

Examples of nucleotide sequence of DNA fragment containing glnA2 according to the present invention, which is obtained as described above, and amino acid sequence that can be encoded by the sequence are shown as SEQ ID NO: 1. Further, only an amino acid sequence of protein having glutamine synthetase activity, which is encoded by glnA2, is shown in SEQ ID NO: 2.

Further, in the aforementioned DNA fragment, another ORF was found immediately downstream from ORF of the glnA2 gene. Based on homology comparison with respect to known sequences, that ORF was expected to be a gene (glnE) coding for a protein having glutamine synthetase adenylyl transferase activities (ATase). Only the amino acid sequence of the protein having the ATase activity is shown as SEQ ID NO: 3.

Nucleotide sequences of the DNA fragments containing glnA2 or glnE according to the present invention were clarified by the present invention. Therefore, they can be isolated from chromosomal DNA of *Brevibacterium lactofermentum* by the PCR method using primers produced based on the nucleotide sequences.

The first DNA of the present invention may be one coding for glutamine synthetase including substitution, deletion, insertion, addition or inversion of one or several amino acids at one or more sites, so long as the glutamine synthetase activity of the encoded protein is not defected. Although the number of "several" amino acids referred to herein differs depending on position or type of amino acid residues in the three-dimensional structure of the protein, it may be specifically 2 to 90, preferably 2 to 50, more preferably 2 to 20.

The second DNA of the present invention may be one coding for glutamine synthetase adenylyl transferase including substitution, deletion, insertion, addition or inversion of one or several amino acids at one or more sites, so long as the glutamine synthetase adenylyl transferase activities of the encoded protein are not defected. Although the number of "several" amino acids referred to herein differs depending on position or type of amino acid residues in the three-dimensional structure of the protein, it may be specifically 2 to 350, preferably 2 to 50, more preferably 2 to 20. Even in a case that the glutamine synthetase and adenylyl transferase activities are impaired, such a DNA fall within the scope of the present invention so long as it causes homologous recombination.

A DNA coding for the substantially same protein as the aforementioned GS or ATase can be obtained by, for example, modifying the nucleotide sequence of glnA2 or glnE by means of the site-directed mutagenesis method so that one or more amino acid residues at a specified site should involve substitution, deletion, insertion, addition or inversion. A DNA modified as described above may also be obtained by a conventionally known mutagenesis treatment. The mutagenesis treatment includes a method of treating a DNA before the mutagenesis treatment in vitro with hydroxylamine or the like, and a method for treating a microorganism such as an genus Escherichia harboring a DNA before the mutagenesis treatment by ultraviolet irradiation or with a mutagenizing agent used for a usual mutagenesis treatment such as N-methyl-N'-nitro-N-nitrosoguanidine (NTG) and nitrous acid.

A DNA coding for substantially the same protein as glutamine synthetase or glutamine synthetase adenylyl transferase can be obtained by expressing a DNA having such a mutation as described above in an appropriate cell, and investigating activity of an expressed product. A DNA coding for substantially the same protein as GS or ATase can also be obtained by isolating a DNA that is hybridizable with a probe having a nucleotide sequence comprising, for example, the nucleotide sequence corresponding to nucleotide numbers of 659 to 1996 or 2066 to 5200 of the nucleotide sequence shown in Sequence Listing as SEQ ID NO: 1, under the stringent conditions, and codes for a protein having the glutamine synthetase or a protein having the glutamine synthetase adenylyl transferase activity, from DNA coding for glutamine synthetase or glutamine synthetase and adenylyl transferase having a mutation or from a cell harboring it. The "stringent conditions" referred to herein is a condition under which so-called specific hybrid is formed, and non-specific hybrid is not formed. It is difficult to clearly express this condition by using any numerical value. However, for example, the stringent conditions are exemplified by a condition under which DNAs having high homology, for example, DNAs having homology of not less than 50% are hybridized with each other, but DNAs having homology lower than the above are not hybridized with each other. Alternatively, the stringent conditions are exemplified by a condition under which DNAs are hybridized with each other at a salt concentration corresponding to an ordinary condition of washing in Southern hybridization, i.e., 1×SSC, 0.1% SDS, preferably 0.1×SSC, 0.1% SDS, at 60° C.

As a probe, a partial sequence of the nucleotide sequence of SEQ ID NO: 1 can also be used. Such a probe may be prepared by PCR using oligonucleotides produced based on the nucleotide sequence of SEQ ID NO: 1 as primers, and a DNA fragment containing the nucleotide sequence of SEQ ID NO: 1 as a template. When a DNA fragment in a length of about 300 bp is used as the probe, the conditions of washing for the hybridization consist of, for example, 50° C., 2×SSC and 0.1% SDS.

Genes that are hybridizable under such conditions as described above includes those having a stop codon in the genes, and those having no activity due to mutation of active center. However, such mutation can be easily removed by ligating each gene with a commercially available activity expression vector, and measuring the glutamine synthetase or glutamine synthetase adenylyl transferase activities. The glutamine synthetase activity can be measured by, for example, the method described in *Methods in Enzymology*, Vol. XVIIA, 910–915, ACADEMIC PRESS (1970), and the glutamine synthetase adenylyl transferase activities can be measured by, for example, the method described in *Methods in Enzymology*, Vol. XVIIA, 922–923, ACADEMIC PRESS (1970). Even a DNA coding for glutamine synthetase adenylyl transferase of which activities are reduced or deleted can also be used in the present invention.

Specific examples of the DNA coding for a protein substantially the same as GS include DNA coding for a protein that has homology of preferably 80% or more, more preferably 85% or more, still more preferably 90% or more, with respect to the amino acid sequence shown as SEQ ID NO: 2 and has GS activity. Specific examples of the DNA coding for a protein substantially the same as ATase include DNA coding for a protein that has homology of preferably 65% or more, more preferably 80% or more, still more preferably 90% or more, with respect to the amino acid sequence shown as SEQ ID NO: 3 and has ATase activity.

BEST MODE FOR CARRYING OUR THE INVENTION

Hereafter, the present invention will be explained more specifically with reference to the following examples.

EXAMPLE 1

Evaluation of GS Gene-Amplified Strain (1) Cloning of glnA Gene of Coryneform Bacterium The glnA sequence of *Corynebacterium glutamicum* had been already clarified (*FEMS Microbiology Letters*, 81–88, (154) 1997). Based on the reported nucleotide sequence, the primers shown in Sequence Listing as SEQ ID NOS: 4 and 5 were synthesized, and a glnA fragment was amplified by the PCR method using chromosome DNA of *Brevibacterium flavum* ATCC 14067 strain as a template.

The chromosomal DNA of *Brevibacterium flavum* ATCC 14067 strain was prepared by using Bacterial Genome DNA Purification Kit (Advanced Genetic Technologies Corp.). PCR was performed for 30 cycles each consisting of reactions at 94° C. for 30 seconds for denaturation, at 55° C. for 15 seconds for annealing and 72° C. for 2 minutes for extension by using Pyrobest DNA Polymerase (Takara Shuzo).

The produced PCR product was purified in a conventional manner, digested with a restriction enzyme SalI, ligated with pMW219 (Nippon Gene) digested with SalI by using a ligation kit (Takara Shuzo), and used to transform competent cells of *Escherichia coli* JM109 (Takara Shuzo). The cells were plated on L medium containing 10 μg/ml of IPTG, 40 μg/ml of X-Gal and 25 μg/ml of kanamycin and cultured overnight. Then, the appeared white colonies were picked up and separated into single colonies to obtain transformants.

Plasmids are prepared from the transformants by the alkali method, and a plasmid in which the glnA gene was inserted into the vector was designated as pMW219GS.

(2) Construction of Plasmid Having glnA and Replication Origin of Coryneform Bacteria Further, in order to construct a plasmid having the glnA gene and a replication origin of coryneform bacteria, the plasmid pHK4 (refer to Japanese Patent Laid-open Publication No. 5-7491) containing replication origin of the plasmid pHM1519 (*Agric. Biol. Chem.*, 48, 2901–2903 (1984)) that had been already obtained and was autonomously replicable in coryneform bacteria was digested with restriction enzymes BamHI and KpnI to obtain a gene fragment containing the replication origin. The obtained fragment was blunt-ended by using DNA Blunt-ending Kit (Takara Shuzo) and inserted into the KpnI site of pMW219GS using a KpnI linker (Takara Shuzo). This plasmid was designated as pGS.

(3) Introduction of pGS into Coryneform Bacterium and Evaluation of Culture

An L-glutamine producing bacterium, *Brevibacterium flavum* AJ12418 (FERM BP-2205: refer to Japanese Patent Laid-open Publication No. 2-186994), was transformed with the plasmid pGS by the electric pulse method (refer to Japanese Patent Laid-open Publication No. 2-207791) to obtain a transformant. By using the obtained transformant AJ12418/pGS, culture for L-glutamine production was performed as follows.

Cells of AJ12418/pGS strain obtained by culture on a CM2B plate medium containing 25 μg/ml of kanamycin were inoculated into a medium containing 100 g of glucose, 60 g of $(NH_4)_2SO_4$, 2.5 g of $KH_2PO_4$, 0.4 g of $MgSO_4 \cdot 7H_2O$, 0.01 g of $FeSO_4 \cdot 7H_2O$, 350 μg of $VB_1$-HCl, 4 μg of biotin, 200 mg of soybean hydrolysates and 50 g of $CaCO_3$ in 1 L of pure water (adjusted to pH 6.8 with NaOH) and cultured at 31.5° C. with shaking until the sugar in the medium was consumed.

After the completion of the culture, the amount of accumulated L-glutamine in the culture broth was analyzed by liquid chromatography for appropriately diluted culture broth. CAPCELL PAK C18 (Shiseido) was used as a column, and the sample was eluted with an eluent containing 0.095% phosphoric acid, 3.3 mM heptanesulfonic acid and 5% acetonitrile in 1 L of distilled water. The accumulated L-glutamine amount was analyzed based on variation of absorbance at 210 nm. The results of this analysis are shown in Table 1.

TABLE 1

| Strain | L-Gln (g/L) | L-Glu (g/L) | Culture time (hr) |
|---|---|---|---|
| AJ12418 | 38.4 | 0.7 | 70 |
| AJ12418/pGS | 45.1 | 0.02 | 82 |

In the pGS-introduced strain, accumulation of L-glutamine (L-Gln) was markedly improved, and by-production of L-glutamic acid (L-Glu) was considerably suppressed. From these results, it was demonstrated that enhancement of GS was effective for improvement of yield in the production of L-glutamine. The data for the enzymatic activity of GS are shown in Table 2 of Example 2.

EXAMPLE 2

Evaluation of GS Adenylylation Site-Modified Strain (1) Construction of Adenylylation Site-Modified Plasmid The adenylylation site of glnA gene product of coryneform bacteria had been already clarified (*FEMS Microbiology Letters*, 303–310, (173) 1999). Therefore, an adenylylation site-modified strain was obtained by replacing the glnA gene on the chromosome with a glnA gene of which adenylylation site was modified. Specific procedures will be described below.

First, PCR was performed by using chromosome DNA of *Brevibacterium flavum* ATCC 14067 strain as a template and the synthetic DNAs shown in Sequence Listing as SEQ ID NOS: 6 and 7 as primers to obtain an amplification product for the N-terminus side of the glnA gene. Separately, in order to obtain an amplification product for the C-terminus side of the glnA gene, PCR was performed by using chromosome DNA of *Brevibacterium flavum* ATCC 14067 strain as a template and the synthetic DNAs shown in Sequence Listing as SEQ ID NOS: 8 and 9 as primers. Since mismatches were introduced into the sequences shown in Sequence Listing as SEQ ID NOS: 7 and 8, a mutation was introduced into the terminal portion of each of the amplification products. Then, in order to obtain a glnA gene fragment introduced with a mutation, PCR was performed by using the aforementioned gene products for N- and C-terminus sides of glnA mixed in equimolar amounts as a template and the synthetic DNAs shown in Sequence Listing as SEQ ID NOS: 10 and 11 as primers to obtain a glnA gene amplification product introduced with a mutation at the adenylylation site. The produced PCR product was purified in a conventional manner, digested with HincII and inserted into the HincII site of pHSG299 (Takara Shuzo). This plasmid was designated as pGSA.

(2) Construction of Adenylylation Site-Modified Strain and Evaluation of Culture Since the above pGSA does not contain a region that enables its autonomous replication within cells of coryneform bacteria, when a coryneform bacterium is transformed with this plasmid, a strain in which the plasmid is incorporated into chromosome by homologous recombination is obtained as a transformant although it occurs at an extremely low frequency.

The L-glutamine producing bacterium, *Brevibacterium flavum* AJ12418, was transformed with the plasmid pGSA at a high concentration by the electric pulse method (refer to Japanese Patent Laid-open Publication No. 2-207791), and transformants were obtained by using kanamycin resistance as a marker. Then, these transformants were subcultured and strains that became kanamycin sensitive were obtained. Further, the sequences of glnA gene of the kanamycin sensitive strains were determined, and a strain in which the adenylylation site in the sequence was replaced with that region of glnA derived from pGSA was designated as QA-1. Culture for L-glutamine production was performed in the same manner as described in Example 1, (3) using AJ12418, AJ12418/pGS and QA-1 strains. The results are shown in Table 2.

TABLE 2

| Strain | L-Gln (g/L) | GS activity (U/mg) | Culture time (hr) |
|---|---|---|---|
| AJ12418 | 39.0 | 0.030 | 70 |
| AJ12418/pGS | 46.1 | 0.067 | 81 |
| QA-1 | 44.3 | 0.040 | 72 |

For the QA-1 strain, improvement of L-glutamine accumulation was observed compared with AJ12418.

The results for measurement of GS activity of these strains are also shown in Table 2. The GS activity was measured by adding a crude enzyme solution to a solution containing 100 mM imidazole-HCl (pH 7.0), 0.1 mM $NH_4Cl$, 1 mM $MnCl_2$, 1 mM phosphoenolpyruvic acid, 0.3 mM NADH, 10 U of lactate dehydrogenase, 25 U of pyruvate kinase, 1 mM ATP and 10 mM MSG and measuring variation of absorbance at 340 nm at 30° C. referring to the method described in *Journal of Fermentation and Bioengineering*, Vol. 70, No. 3, 182–184, 1990. For the measurement of blank, the aforementioned reaction solution not containing MSG was used. The crude enzyme solution was prepared by separating cells from the aforementioned culture broth by centrifugation, washing the cells with 100 mM imidazole-HCl (pH 7.0), sonicating the cells and removing undisrupted cells and unsoluble protein by centrifugation. Protein concentration of the crude enzyme solution was quantified with Protein Assay (Bio-Rad) by using bovine serum albumin as a standard sample.

EXAMPLE 3

Evaluation of GDH Gene-Amplified Strain (1) Construction of gdh-Amplified Strain and Evaluation of Culture Construction of a plasmid pGDH into which the gdh gene of coryneform bacteria was cloned was performed as follows. First, chromosome DNA of *Brevibacterium lactofermentum* ATCC 13869 strain was extracted, and PCR was performed by using the chromosome DNA as a template and the synthetic DNAs shown in Sequence Listing as SEQ ID NOS: 12 and 13 as primers. The obtained DNA fragment was blunt-ended and inserted into the SmaI site of pHSG399 (Takara Shuzo). This plasmid was designated as pHSG399GDH.

Then, a replication origin derived from the plasmid pHM1519 (*Agric. Biol. Chem.*, 48, 2901–2903 (1984)) that could autonomously replicate in coryneform bacteria was introduced into the SalI site of pHSG399GDH. Specifically, the aforementioned pHK4 was digested with restriction enzymes BamHI and KpnI to obtain a gene fragment containing the replication origin, and the obtained fragment was blunt-ended and inserted into the SalI site of pHSG399GDH by using an SalI linker (Takara Shuzo). This plasmid was designated as pGDH.

The L-glutamine producing bacterium, *Brevibacterium flavum* AJ12418 strain, was transformed with pGDH to obtain a transformant. Culture for L-glutamine production was performed by the method described in Example 1 using the obtained transformant AJ12418/pGDH. The results are shown in Table 3. In the GDH-enhanced strain, yield of L-glutamine decreased and by-production of L-glutamic acid increased, but culture time was considerably shortened.

TABLE 3

| Strain | L-Gln (g/L) | L-Glu (g/L) | Culture time (hr) |
|---|---|---|---|
| AJ12418 | 38.4 | 0.7 | 70 |
| AJ12418/pGDH | 29.5 | 12.0 | 55 |

EXAMPLE 4

Construction and Evaluation of Strain in which GS and GDH are Enhanced Simultaneously (1) Construction of gdh Promoter-Modified Plasmid Chromosomal DNA of *Brevibacterium flavum* ATCC 14067 strain was extracted, and PCR was performed by using the chromosomal DNA as a template and the synthetic DNAs shown in Sequence Listing as SEQ ID NOS: 14 and 15 as primers. The obtained DNA fragment was digested with restriction enzymes StuI and PvuII and inserted into the SmaI site of pHSG399. This plasmid was digested with a restriction enzyme SacI to obtain a DNA fragment containing the gdh promoter and a partial fragment of the gdh gene, and it was inserted into the SacI site of pKF19k (Takara Shuzo). This plasmid was designated as pKF19GDH.

A mutation was introduced into the promoter region by using Mutan-Super Express Km (Takara Shuzo). LA-PCR was performed by using pkF19GDH as a template, a selection primer attached to Mutan-super Express Km and a 5'-end phosphorylated synthetic DNA shown in Sequence Listing as SEQ ID NO: 16 or 17 as a primer for mutagenesis. The reaction product was purified by ethanol precipitation, and competent cells of *Escherichia coli* MV1184 (Takara Shuzo) were transformed with the product to obtain transformants.

Plasmids were extracted from the transformants, and sequences of the gdh promoter region were determined. Among these, those having the sequences shown in Table 4 were designated as pKF19GDH1 and pKF19GDH4. It is expected that the GDH activity can be improved by about 3 times by replacing the gdh promoter sequence with that of pKF19GDH1 type, or by about 5 times by replacing the gdh promoter sequence with that of pKF19GDH4 type, compared with gdh having a promoter of a wild-type (refer to International Patent Publication WO00/18935).

These plasmids were digested with a restriction enzyme SacI to obtain a DNA fragment containing the gdh promoter and a partial fragment of the gdh gene, and it was inserted into the SacI site of pSFKT2 (refer to Japanese Patent Laid-open Publication No. 2000-262288). These plasmids were designated as pSFKTGDH1 and pSFKTGDH4, respectively. pSFKT2 was a derivative of the plasmid pAM330 derived from the *Brevibacterium lactofermentum* ATCC 13869 strain, and it is a plasmid of which autonomous replication in coryneform bacteria has become temperature sensitive.

TABLE 4

| Plasmid | gdh promoter sequence |
|---|---|
| pKF19GDH | TGGTCAtatctgtgcgacgctgcCATAAT (SEQ ID NO: 20) |
| pKF19GDH1 | TGGTCAtatctgtgcgacgctgcTATAAT (SEQ ID NO: 21) |
| pKF19GDH4 | TTGCCAtatctgtgcgacgctgcTATAAT (SEQ ID NO: 22) |

(2) Introduction of gdh Promoter Mutation Into Chromosome

A mutation was introduced into the gdh promoter sequence on chromosome as follows. First, the QA-1 strain was transformed with the plasmid pSFKTGDH1 or pSFKTGDH4 by the electric pulse method to obtain a transformant, respectively. After the transformation, culture was performed at 25° C. Then, these transformants were cultured at 34° C., and strains showing kanamycin resistance at 34° C. were selected. Since the aforementioned plasmids cannot autonomously replicate at 34° C., only those in which these plasmids were integrated into chromosome by homologous recombination show kanamycin resistance. Further, the strains in which these plasmids were integrated into chromosome were cultured in the absence of kanamycin, and strains that became kanamycin sensitive were selected. Among those, strains in which the same mutation as that of pSFKTGDH1 or pSFKTGDH4 was introduced into the gdh promoter region on the chromosome were designated as QB-1 and QB-4, respectively.

(3) Construction of gdh Gene-Amplified Strain and Measurement of GDH Activity

The L-glutamine producing bacterium, *Brevibacterium flavum* QA-1 strain, was transformed with the plasmid pGDH described in Example 3, (2) to obtain a transformant. Culture for L-glutamine production was performed by the method described in Example 1 using the obtained transformant QA-1/pGDH. The GDH activity was measured by adding a crude enzyme solution to a solution containing 100 mM Tris-HCl (pH 7.5), 20 mM NH$_4$Cl, 10 mM α-ketoglutaric acid and 0.25 mM NADPH and measuring change of absorbance at 340 nm referring to *Mol. Microbiology*, 317–326 (6) 1992. The crude enzyme solution was prepared by separating cells from the aforementioned culture broth by centrifugation, washing the cells with 100 mM Tris-HCl (pH 7.5), sonicating the cells and removing undisrupted cells by centrifugation. Protein concentration of the crude enzyme solution was quantified with Protein Assay (Bio-Rad) by using bovine serum albumin as a standard sample. The results are shown in Table 5.

As for yield of L-glutamine, the GDH promoter-modified strains, QB-1 and QB-4, showed high yield. Further, the QA-1/pGDH strain also showed higher yield than that obtained with the AJ12418 strain. The culture time of the QA-1/pGDH strain was the shortest. The by-production of L-glutamic acid was markedly improved in the QB-1 and QB-4 strains. From these results, it was demonstrated that the simultaneous enhancement of GS and GDH was effective for improvement of yield of L-glutamine and shortening of culture time.

TABLE 5

| Strain | L-Gln (g/L) | L-Glu (g/L) | Culture time (hr) | GDH activity (U/mg) |
|---|---|---|---|---|
| AJ12418 | 40.5 | 0.8 | 68 | 1.6 |
| QA-1/PGDH | 47.9 | 1.0 | 60 | 15.2 |
| QB-1 | 50.5 | 0.1 | 65 | 4.2. |
| QB-4 | 50.0 | 0.3 | 65 | 9.6 |

EXAMPLE 5

Acquisition of Gene Coding for Isozyme of GS

In the paper that reported acquisition of glnA of *Corynebacterium glutamicum* (*FEMS Microbiol. Letter*, 154 (1997) 81–88), it is described that a ΔglnA-disrupted strain became to show glutamine auxotrophy and lost the GS activity, and it also reported data showing results of Southern blotting and suggesting existence of an isozyme. Further, "Amino Acid Fermentation", Japan Science Societies Publication (Gakkai Shuppan Center), pp.232–235 describes that there are two kinds of GS for *Corynebacterium glutamicum*. Therefore, it was attempted to obtain a gene coding for the second GS isozyme.

(1) Preparation of Probe

A gene coding for an isozyme of GS (glnA2) was obtained by colony hybridization. First, PCR was performed by using the primers shown in Sequence Listing as SEQ ID NOS: 18 and 19 and chromosomal DNA of the *Brevibacterium lactofermentum* ATCC 13869 strain as a template to obtain a partial fragment of the glnA gene. This DNA fragment was labeled by using DIG-High Prime DNA Labeling & Detection Starter Kit I (Boehringer Mannheim) and used as a probe.

(2) Colony Hybridization

Chromosomal DNA of the *Brevibacterium lactofermentum* ATCC 13869 strain was extracted and partially digested with a restriction enzyme Sau3AI, and the obtained DNA fragment was inserted into the BamHI site of the vector of pHSG299 and used to transform the *Escherichia coli* JM109 strain. The obtained transformant was transferred to Hybond-N+ (Amersham Pharmacia Biotech), denatured, neutralized and then hybridized with the probe prepared in Example 5, (1) by using DIG-High Prime DNA Labeling & Detection Starter Kit I. At this time, a transformant that hybridized strongly and a transformant that hybridized weakly were recognized. Plasmid DNAs were prepared from these transformants and nucleotide sequences of inserts were determined. As a result, clones containing a gene showing high homology with respect to a known glutamine synthetase of coryneform bacteria could be obtained. The total nucleotide sequence of the insert of the latter was shown in Sequence Listing as SEQ ID NO: 1.

Open reading frames were deduced, and amino acid sequences deduced from the nucleotide sequences were shown in Sequence Listing as SEQ ID NOS: 2 and 3. Each of these amino acid sequences was compared with known sequences for homology. The used database was Genbank. As a result, it became clear that the amino acid sequences encoded by the both of the open reading frames were novel proteins of coryneform bacteria.

The nucleotide sequences and the amino acid sequences were analyzed by using Genetyx-Mac computer program (Software Development, Tokyo). The homology analysis was performed according to the method of Lipman and Pearson (*Science,* 227, 1435–1441, 1985).

The amino acid sequence shown in Sequence Listing as SEQ ID NO: 2 showed 34.6%, 65.6% and 60% of homology with respect to already reported GS of *Corynebacterium glutamicum* (*FEMS Microbiology Letters,* 81–88, (154) 1997), GS of *Mycobacterium tuberculosis* (GenBank accession Z70692) and GS of *Streptomyces coelicolor* (GenBank accession AL136500), respectively (Table 6), and it was found to be an isozyme of GS of coryneform bacteria.

On the other hand, the sequence shown in Sequence Listing as SEQ ID NO: 3 showed 51.9% and 33.4% of homology with respect to the already reported ATase of *Mycobacterium tuberculosis* (GenBank accession Z70692) and ATase of *Streptomyces coelicolor* (GenBank accession Y17736 (SEQ ID NO: 25)), respectively (Table 7), and it was found to be ATase of coryneform bacteria. Therefore, it was found that, in the nucleotide sequence shown as SEQ ID NO: 1, the open reading frame coding for the amino acid sequence shown as SEQ ID NO: 2 was glnA2, and the open reading frame coding for the amino acid sequence shown as SEQ ID NO: 3 was glnE.

TABLE 6

| Strain | Gene name | Amino acid Number | Homology |
|---|---|---|---|
| *Brevibacterium lactofermentum* | glnA2 | 446 A.A. | — |
| *Corynebacterium glutamicum* | glnA | 478 A.A. | 34.6% |
| *Mycobacterium tuberculosis* | glnA2 | 446 A.A. | 65.6% |
| *Streptomyces coelicolor* | glnA | 453 A.A. | 60.0% |

TABLE 7

| Strain | Gene name | Amino acid Number | Homology |
|---|---|---|---|
| *Brevibacterium lactofermentum* | glnE | 1045 A.A. | — |
| *Mycobacterium tuberculosis* | glnE | 994 A.A. | 51.9% |
| *Streptomyces coelicolor* | glnE | 784 A.A. | 33.4% |

EXAMPLE 6

Production of L-glutamine by ATase-Deficient Strain

Since the gene glnE coding for ATase was elucidated in the aforementioned Example 5, a glnE-deficient strain was constructed from the L-glutamine producing bacterium AJ12418. The specific procedure will be shown below.

First, PCR was performed by using chromosome DNA of *Brevibacterium flavum* ATCC 14067 strain as a template and the synthetic DNAs of SEQ ID NOS: 23 and 24 as primers to obtain a partial fragment of glnE gene. The produced PCR product was purified in a conventional manner, then blunt-ended and inserted into the HincII site of pHSG299 (Takara Shuzo). This plasmid was designated as pGLNE. Then, in order to delete a partial region of the glnE gene in this plasmid, pGLNE was digested with HincII and self-ligated, and the obtained plasmid was designated as pΔGLNE. This plasmid contained the 2341st to 4650th nucleotides of the nucleotide sequence shown in Sequence Listing as SEQ ID NO: 1, but it had deletion of about 300 bp from the 3343rd HincII recognition site to the 3659th HincII recognition site.

Since the above pΔGLNE does not contain a region that enables its autonomous replication within cells of coryneform bacteria, when a coryneform bacterium is transformed with this plasmid, a strain in which the plasmid is integrated into chromosome by homologous recombination may be produced as a transformant although it occurs at an extremely low frequency.

The L-glutamine producing bacterium, *Brevibacterium flavum* AJ12418, was transformed with the plasmid pΔGLNE at a high concentration by the electric pulse method, and transformants were obtained by using kanamycin resistance as a marker. Then, these transformants were subcultured to obtain strains that became kanamycin sensitive. Further, chromosomal DNAs of the obtained kanamycin sensitive strains were extracted, and PCR was performed by using each chromosomal DNA as a template and the synthetic DNAs shown in Sequence Listing as SEQ ID NOS: 23 and 24 as primers to obtain partial fragments of the glnE gene. A strain of which PCR product did not provide about 300 bp fragment when it was digested with HincII was determined as a glnE-disrupted strain. This strain was designated as QA-T. Culture for L-glutamine production was performed in the same manner as described in Example 1, (3) by using AJ12418 and QA-T strains. The results are shown in Table 8.

The QA-T strain showed improvement of L-glutamine accumulation compared with the AJ12418 strain. The results of measurement of the GS activity of these strains are also shown in Table 8. It was confirmed that the GS activity was improved in the QA-T strain compared with the AJ12418 strain.

TABLE 8

| Strain | L-Gln (g/L) | GS activity (U/mg) | Culture time (hr) |
|---|---|---|---|
| AJ12418 | 39.0 | 0.03 | 70 |
| QA-T | 45.1 | 0.05 | 75 |

(Explanation of Sequence Listing)

SEQ ID NO: 1: glnA2 And glnE nucleotide sequences
SEQ ID NO: 2: glnA2 amino acid sequence
SEQ ID NO: 3: glnE amino acid sequence
SEQ ID NO: 4: Primer N for glnA amplification
SEQ ID NO: 5: Primer C for glnA amplification
SEQ ID NO: 6: glnA 1st PCR primer NN
SEQ ID NO: 7: glnA 1st PCR primer NC
SEQ ID NO: 8: glnA 1st PCR primer CN
SEQ ID NO: 9: glnA 1st PCR primer CC
SEQ ID NO: 10: glnA 2nd PCR primer N
SEQ ID NO: 11: glnA 2nd PCR primer C
SEQ ID NO: 12: Primer N for gdh amplification
SEQ ID NO: 13: Primer C for gdh amplification
SEQ ID NO: 14: Primer N2 for gdb amplification
SEQ ID NO: 15: Primer C2 for gdb amplification
SEQ ID NO: 16: Primer M1 for gdh promoter mutation
SEQ ID NO: 17: Primer M4 for gdh promoter mutation
SEQ ID NO: 18: Primer N for glnA probe preparation
SEQ ID NO: 19: Primer C for glnA probe preparation
SEQ ID NO: 20: Wild-type gdh promoter sequence
SEQ ID NO: 21: Mutant type gdh promoter sequence
SEQ ID NO: 22: Mutant type gdh promoter sequence
SEQ ID NO: 23: Primer N for glnE disruption
SEQ ID NO: 24: Primer C for glnE disruption

SEQUENCE LISTING

<160> NUMBER OF SEQ ID NOS: 25

<210> SEQ ID NO 1
<211> LENGTH: 5500
<212> TYPE: DNA
<213> ORGANISM: Brevibacterium lactofermentum
<220> FEATURE:
<221> NAME/KEY: CDS
<222> LOCATION: (659)..(1996)
<223> OTHER INFORMATION:
<220> FEATURE:
<221> NAME/KEY: CDS
<222> LOCATION: (2006)..(5200)
<223> OTHER INFORMATION:

<400> SEQUENCE: 1

```
gatcagtgct tcggcttctt cttcgaagtt ggtggactct gccttttca aaagtgcggt      60 gatacgatga tgcgctttgg cctgtgccgg ggtcattggg ctggtgtctt gattgtctaa     120
ggcgtggagc tctgcgagca ttgcccagtc aggcaaggta cttagcttcg gtagctcggt    180
gagaatcttc tccagggtca tcaccggcaa gtggctagtt tcggcggcac gcgttccgtt    240
cacccacagt gtgtacatct catcggagca ggagtaagca atctcaggta gcgcgtgaaa    300
caggagtgga tcaatatcgg cggaaaactc atggcggaga tcggcgggag tccacccacg    360
aagcgcacag aaacctaggt ggctgatgat gctttcttct aaaatctgac ggtaagagtc    420
ttgtgcgtcg gtgacgttgt cggagaagtg ggagagggtc attgcggttt ccttattcgt    480
aggagagttc taatttcggt gcggttctca gtgaaccacc caagctggac acctcccacc    540
cccgtgtcat caaaaaaccg cgacatcctt gagtaactct gagaaaaact accccccgatg    600 cgagtataaa agtggcaaat gcgcagtcga tgtcccatcg ctgcgtagat tagttttc    658
```

| atg | aac | agc | gaa | cag | gaa | ttt | gta | ctc | agc | gcc | att | gaa | gaa | cgc | gac | 706 |
|---|---|---|---|---|---|---|---|---|---|---|---|---|---|---|---|---|
| Met | Asn | Ser | Glu | Gln | Glu | Phe | Val | Leu | Ser | Ala | Ile | Glu | Glu | Arg | Asp | |
| 1 | | | | 5 | | | | | 10 | | | | | 15 | | |

| att | aag | ttt | gtg | cgt | cta | tgg | ttc | act | gac | att | ctt | gga | cac | ttg | aag | 754 |
|---|---|---|---|---|---|---|---|---|---|---|---|---|---|---|---|---|
| Ile | Lys | Phe | Val | Arg | Leu | Trp | Phe | Thr | Asp | Ile | Leu | Gly | His | Leu | Lys | |
| | | | 20 | | | | | 25 | | | | | 30 | | | |

| tca | gtt | gtt | gtg | gct | cct | gca | gaa | cta | gag | tct | gcg | ttg | gaa | gaa | ggc | 802 |
|---|---|---|---|---|---|---|---|---|---|---|---|---|---|---|---|---|
| Ser | Val | Val | Val | Ala | Pro | Ala | Glu | Leu | Glu | Ser | Ala | Leu | Glu | Glu | Gly | |
| | | 35 | | | | | 40 | | | | | 45 | | | | |

| atc | gga | ttc | gat | ggc | tca | gcc | att | gag | ggc | tac | gcg | cgt | atc | tcg | gaa | 850 |
|---|---|---|---|---|---|---|---|---|---|---|---|---|---|---|---|---|
| Ile | Gly | Phe | Asp | Gly | Ser | Ala | Ile | Glu | Gly | Tyr | Ala | Arg | Ile | Ser | Glu | |
| 50 | | | | | 55 | | | | | 60 | | | | | | |

| gcg | gac | acc | att | gcc | cgc | cca | gat | cca | tcg | aca | ttc | cag | gtc | ctc | cca | 898 |
|---|---|---|---|---|---|---|---|---|---|---|---|---|---|---|---|---|
| Ala | Asp | Thr | Ile | Ala | Arg | Pro | Asp | Pro | Ser | Thr | Phe | Gln | Val | Leu | Pro | |
| 65 | | | | 70 | | | | | 75 | | | | | 80 | | |

| cta | gaa | gcg | ggc | atc | tca | aaa | ctg | cag | gca | gca | cgc | ctg | ttt | tgc | gat | 946 |
|---|---|---|---|---|---|---|---|---|---|---|---|---|---|---|---|---|
| Leu | Glu | Ala | Gly | Ile | Ser | Lys | Leu | Gln | Ala | Ala | Arg | Leu | Phe | Cys | Asp | |
| | | | | 85 | | | | | 90 | | | | | 95 | | |

| gtc | acg | atg | ccg | gac | gga | cag | cca | tct | ttt | tct | gac | ccg | cgc | caa | gtg | 994 |
|---|---|---|---|---|---|---|---|---|---|---|---|---|---|---|---|---|
| Val | Thr | Met | Pro | Asp | Gly | Gln | Pro | Ser | Phe | Ser | Asp | Pro | Arg | Gln | Val | |
| | | | 100 | | | | | 105 | | | | | 110 | | | |

| ctg | cgc | agg | cag | gtc | caa | cta | gct | gca | gat | gaa | ggc | ttg | acc | tgc | atg | 1042 |
|---|---|---|---|---|---|---|---|---|---|---|---|---|---|---|---|---|
| Leu | Arg | Arg | Gln | Val | Gln | Leu | Ala | Ala | Asp | Glu | Gly | Leu | Thr | Cys | Met | |
| | | 115 | | | | | 120 | | | | | 125 | | | | |

| atc | tca | cca | gag | att | gag | ttc | tat | ttg | gtg | caa | agc | ctt | cgc | acc | aac | 1090 |
|---|---|---|---|---|---|---|---|---|---|---|---|---|---|---|---|---|
| Ile | Ser | Pro | Glu | Ile | Glu | Phe | Tyr | Leu | Val | Gln | Ser | Leu | Arg | Thr | Asn | |
| 130 | | | | | 135 | | | | | 140 | | | | | | |

| gga | ctg | cca | cct | gtg | ccc | act | gac | aac | ggc | gga | tat | ttc | gac | caa | gcc | 1138 |
|---|---|---|---|---|---|---|---|---|---|---|---|---|---|---|---|---|

```
                                                              -continued

Gly Leu Pro Pro Val Pro Thr Asp Asn Gly Tyr Phe Asp Gln Ala
145                 150                 155                 160 aca ttc aat gag gcg ccg aat ttc cgt cga aac gcg atg gta gcg ctg    1186
Thr Phe Asn Glu Ala Pro Asn Phe Arg Arg Asn Ala Met Val Ala Leu
                165                 170                 175 gag gaa ctc ggc atc cct gtc gag ttc tcc cac cat gaa act gca cct    1234
Glu Glu Leu Gly Ile Pro Val Glu Phe Ser His His Glu Thr Ala Pro
            180                 185                 190 ggc cag caa gaa atc gat tta cgc cat gcg gat gcg ctc acc atg gcc    1282
Gly Gln Gln Glu Ile Asp Leu Arg His Ala Asp Ala Leu Thr Met Ala
        195                 200                 205 gac aac atc atg acc ttc cgc tac atc atg aaa cag gtg gca agg gac    1330
Asp Asn Ile Met Thr Phe Arg Tyr Ile Met Lys Gln Val Ala Arg Asp
210                 215                 220 caa ggc gtt ggg gca tca ttt atg ccc aag cca ttc caa gaa cat gca    1378
Gln Gly Val Gly Ala Ser Phe Met Pro Lys Pro Phe Gln Glu His Ala
225                 230                 235                 240 ggc tcc gcc atg cac acg cac atg tcc tta ttt gag ggc gat acc aac    1426
Gly Ser Ala Met His Thr His Met Ser Leu Phe Glu Gly Asp Thr Asn
                245                 250                 255 gcg ttc cac gat cca gac gat tct tac atg ctg tcc aaa acc gca aaa    1474
Ala Phe His Asp Pro Asp Asp Ser Tyr Met Leu Ser Lys Thr Ala Lys
            260                 265                 270 cag ttc atc gct gga atc ttg cat cac gct cca gaa ttc acc gct gtg    1522
Gln Phe Ile Ala Gly Ile Leu His His Ala Pro Glu Phe Thr Ala Val
        275                 280                 285 acc aac cag tgg gtc aat tcc tac aaa cgc atc gtg tac gga aac gaa    1570
Thr Asn Gln Trp Val Asn Ser Tyr Lys Arg Ile Val Tyr Gly Asn Glu
290                 295                 300 gct cca act gcg gca acc tgg ggt gta tct aat cgt tct gcg ctg gtt    1618
Ala Pro Thr Ala Ala Thr Trp Gly Val Ser Asn Arg Ser Ala Leu Val
305                 310                 315                 320 cgt gtt cct acc tac cgt ttg aat aag gag gag tcg cgc cgg gtg gag    1666
Arg Val Pro Thr Tyr Arg Leu Asn Lys Glu Glu Ser Arg Arg Val Glu
                325                 330                 335 gtg cgt ctt cct gat acc gct tgt aac cca tat ttg gcg ttt tca gtg    1714
Val Arg Leu Pro Asp Thr Ala Cys Asn Pro Tyr Leu Ala Phe Ser Val
            340                 345                 350 atg ctc ggc gct ggt ttg aaa ggt att aaa gaa ggt tat gag ctc gac    1762
Met Leu Gly Ala Gly Leu Lys Gly Ile Lys Glu Gly Tyr Glu Leu Asp
        355                 360                 365 gag cca gct gag gac gat atc tcc aac ttg agc ttc cgg gaa cgt cgc    1810
Glu Pro Ala Glu Asp Asp Ile Ser Asn Leu Ser Phe Arg Glu Arg Arg
370                 375                 380 gcc atg ggc tac aac gat ctg cca aac agc ctt gat cag gca ctg cgc    1858
Ala Met Gly Tyr Asn Asp Leu Pro Asn Ser Leu Asp Gln Ala Leu Arg
385                 390                 395                 400 caa atg gaa aag tca gag ctt gtt gct gac atc ctc ggt gag cac gtt    1906
Gln Met Glu Lys Ser Glu Leu Val Ala Asp Ile Leu Gly Glu His Val
                405                 410                 415 ttt gag ttt ttc ttg cgc aat aag tgg cgt gaa tgg cgt gac tac caa    1954
Phe Glu Phe Phe Leu Arg Asn Lys Trp Arg Glu Trp Arg Asp Tyr Gln
            420                 425                 430 gag cag atc act ccg tgg gag ctc cga aac aat ctt gat tac tagactttt  2005
Glu Gln Ile Thr Pro Trp Glu Leu Arg Asn Asn Leu Asp Tyr
        435                 440                 445 gca ctc caa tgg aaa ccc tac ggc gac cca att gcg acc cga taa agg    2053
Ala Leu Gln Trp Lys Pro Tyr Gly Asp Pro Ile Ala Thr Arg    Arg
450                 455                 460
```

```
agg gga gaa gct atg tca gga ccg tta aga agt gaa cgt aaa gtc gtt       2101
Arg Gly Glu Ala Met Ser Gly Pro Leu Arg Ser Glu Arg Lys Val Val
            465                 470                 475 ggc ttt gtc aga gac cca ctg cca aaa gtt ggt tct tta tcg ctg aaa       2149
Gly Phe Val Arg Asp Pro Leu Pro Lys Val Gly Ser Leu Ser Leu Lys
        480                 485                 490 tct gag cat gcc caa gca gat cta gag cat ttg ggt tgg cgc aat gtt       2197
Ser Glu His Ala Gln Ala Asp Leu Glu His Leu Gly Trp Arg Asn Val
    495                 500                 505 gag tct ttg gat ttg ttg tgg ggc ttg tca ggt gca ggc gat ccc gat       2245
Glu Ser Leu Asp Leu Leu Trp Gly Leu Ser Gly Ala Gly Asp Pro Asp
510                 515                 520                 525 gtc gcg ctg aac ctt ctt att cgg ctg tat cag gca ctt gaa gca atc       2293
Val Ala Leu Asn Leu Leu Ile Arg Leu Tyr Gln Ala Leu Glu Ala Ile
                530                 535                 540 ggc gag gat gct cga aac gag ctt gat caa gag att cgc cag gat gaa       2341
Gly Glu Asp Ala Arg Asn Glu Leu Asp Gln Glu Ile Arg Gln Asp Glu
            545                 550                 555 gaa cta cga gtc cgc ctt ttt gca ttg ttg ggt ggt tcc tcg gct gtc       2389
Glu Leu Arg Val Arg Leu Phe Ala Leu Leu Gly Gly Ser Ser Ala Val
        560                 565                 570 ggt gat cac ttg gtc gcc aat cct ttg cag tgg aaa ctc tta aaa ctt       2437
Gly Asp His Leu Val Ala Asn Pro Leu Gln Trp Lys Leu Leu Lys Leu
    575                 580                 585 gat gcg cca tcg agg gaa gag atg ttt cag gcg ctg ctg gaa tct gtg       2485
Asp Ala Pro Ser Arg Glu Glu Met Phe Gln Ala Leu Leu Glu Ser Val
590                 595                 600                 605 aaa gct cag cct gct gtg ctt gag gtt gag gat ttc agc gat gca cac       2533
Lys Ala Gln Pro Ala Val Leu Glu Val Glu Asp Phe Ser Asp Ala His
                610                 615                 620 aac att gcc cga gac gat ttg agc acg cct ggt ttt tac acg gct agt       2581
Asn Ile Ala Arg Asp Asp Leu Ser Thr Pro Gly Phe Tyr Thr Ala Ser
            625                 630                 635 gtt acc ggg cct gaa gca gag cga gtc ttg aaa tgg act tat cgc acg       2629
Val Thr Gly Pro Glu Ala Glu Arg Val Leu Lys Trp Thr Tyr Arg Thr
        640                 645                 650 ttg ctg acc cgg att gct gcg cat gat tta gcg ggt acc tat ccc acc       2677
Leu Leu Thr Arg Ile Ala Ala His Asp Leu Ala Gly Thr Tyr Pro Thr
    655                 660                 665 gac atg cgg aga aaa ggt ggc gat cct gtt ccg ttt agc aca gtg acc       2725
Asp Met Arg Arg Lys Gly Gly Asp Pro Val Pro Phe Ser Thr Val Thr
670                 675                 680                 685 atg cag ctc agc gac cta gct gat gct gct ttg act gct gct tta gct       2773
Met Gln Leu Ser Asp Leu Ala Asp Ala Ala Leu Thr Ala Ala Leu Ala
                690                 695                 700 gtg gca att gcc aat gtt tat ggt gaa aag ccg gtt gat tca gct tta       2821
Val Ala Ile Ala Asn Val Tyr Gly Glu Lys Pro Val Asp Ser Ala Leu
            705                 710                 715 tct gtc atc gcg atg ggc aaa tgt ggc gcg cag gaa ttg aac tac att       2869
Ser Val Ile Ala Met Gly Lys Cys Gly Ala Gln Glu Leu Asn Tyr Ile
        720                 725                 730 tca gat gtg gac gtg gtg ttt gtt gca gag ccg gca aac tct aaa tca       2917
Ser Asp Val Asp Val Val Phe Val Ala Glu Pro Ala Asn Ser Lys Ser
    735                 740                 745 aca cgc acc gca gca gag ctc att cgc atc ggt agc aac tcg ttc ttt       2965
Thr Arg Thr Ala Ala Glu Leu Ile Arg Ile Gly Ser Asn Ser Phe Phe
750                 755                 760                 765 gag gtg gat gca gca ctt cgc cca gaa ggt aaa agt ggc gct ctt gtg       3013
Glu Val Asp Ala Ala Leu Arg Pro Glu Gly Lys Ser Gly Ala Leu Val
                770                 775                 780
```

```
cgc tct ttg gat tcc cat atg gcg tat tac aag cgc tgg gcg gaa acc    3061
Arg Ser Leu Asp Ser His Met Ala Tyr Tyr Lys Arg Trp Ala Glu Thr
            785                 790                 795 tgg gaa ttt cag gca ctg ctg aaa gct cgt ccc atg acg ggt gat att    3109
Trp Glu Phe Gln Ala Leu Leu Lys Ala Arg Pro Met Thr Gly Asp Ile
                800                 805                 810 gac ctt ggg cag tcc tat gtg gat gct ctt tca ccg ttg att tgg gcg    3157
Asp Leu Gly Gln Ser Tyr Val Asp Ala Leu Ser Pro Leu Ile Trp Ala
815                 820                 825 gct agc cag cgg gaa tca ttt gtc aca gat gtc caa gct atg cgc cgt    3205
Ala Ser Gln Arg Glu Ser Phe Val Thr Asp Val Gln Ala Met Arg Arg
830                 835                 840                 845 cga gtg ttg gac aat gtt ccg gaa gac ttg cgt gat cgt gag ctg aag    3253
Arg Val Leu Asp Asn Val Pro Glu Asp Leu Arg Asp Arg Glu Leu Lys
                850                 855                 860 ctt ggt cgc ggt ggt ttg agg gat gtg gag ttt gct gtc cag ctc ctt    3301
Leu Gly Arg Gly Gly Leu Arg Asp Val Glu Phe Ala Val Gln Leu Leu
                865                 870                 875 cag atg gtg cat ggt cgc att gat gag acg ttg cgg gtt cgg tca acg    3349
Gln Met Val His Gly Arg Ile Asp Glu Thr Leu Arg Val Arg Ser Thr
            880                 885                 890 gta aat gct ttg cat gtg ttg gtt gat cag gga tat gtg ggt cgt gaa    3397
Val Asn Ala Leu His Val Leu Val Asp Gln Gly Tyr Val Gly Arg Glu
            895                 900                 905 gac ggg cat aat ctc att gag tcg tat gag ttt ttg cgc ctg ttg gag    3445
Asp Gly His Asn Leu Ile Glu Ser Tyr Glu Phe Leu Arg Leu Leu Glu
910                 915                 920                 925 cat cgc ctt caa ttg gag cgg atc aag cgc act cac ttg tta ccg aaa    3493
His Arg Leu Gln Leu Glu Arg Ile Lys Arg Thr His Leu Leu Pro Lys
                930                 935                 940 cct gat gac cga atg aat atg cgc tgg ttg gcg cgc gct tct ggg ttt    3541
Pro Asp Asp Arg Met Asn Met Arg Trp Leu Ala Arg Ala Ser Gly Phe
                945                 950                 955 act ggt tcg atg gag caa agt tcg gcc aaa gct atg gaa cgg cat ttg    3589
Thr Gly Ser Met Glu Gln Ser Ser Ala Lys Ala Met Glu Arg His Leu
            960                 965                 970 cgt aag gtt cgt ttg cag att cag tcg ttg cat agt cag ctg ttt tat    3637
Arg Lys Val Arg Leu Gln Ile Gln Ser Leu His Ser Gln Leu Phe Tyr
975                 980                 985 cgg cca ctg ctg aac tct gtg gtc aac ttg agc gcg gat gcc atc aga   3685
Arg Pro Leu Leu Asn Ser Val Val Asn Leu Ser Ala Asp Ala Ile Arg
990                 995                 1000                1005 ttg tct ccg gat gct  gca aag cta caa ttg  ggg gca ttg gga tac    3730
Leu Ser Pro Asp Ala  Ala Lys Leu Gln Leu  Gly Ala Leu Gly Tyr
                1010                1015                1020 ctg cat cca tca cgt  gct tat gaa cac ctg  act gct ctt gca tca    3775
Leu His Pro Ser Arg  Ala Tyr Glu His Leu  Thr Ala Leu Ala Ser
                1025                1030                1035 gga gct agc cgt aaa  gcc aag att cag gcg  atg ttg ctg ccc acg    3820
Gly Ala Ser Arg Lys  Ala Lys Ile Gln Ala  Met Leu Leu Pro Thr
                1040                1045                1050 ttg atg gag tgg ctg  tct caa aca gct gaa  cca gat gcg gga ttg    3865
Leu Met Glu Trp Leu  Ser Gln Thr Ala Glu  Pro Asp Ala Gly Leu
                1055                1060                1065 ctg aat tac cgc aag  ctt tct gat gct tcc  tat gat cgc agc tgg    3910
Leu Asn Tyr Arg Lys  Leu Ser Asp Ala Ser  Tyr Asp Arg Ser Trp
                1070                1075                1080 ttt ttg cgc atg ctg  cgt gat gag ggc gta  gtg ggg cag cgg ttg    3955
Phe Leu Arg Met Leu  Arg Asp Glu Gly Val  Val Gly Gln Arg Leu
```

-continued

```
                         1085                    1090                    1095
atg cgt att ttg gga  aat tct ccc tat att  tct gaa ctg att atc                4000
Met Arg Ile Leu Gly  Asn Ser Pro Tyr Ile  Ser Glu Leu Ile Ile
                         1100                    1105                    1110 tcc act ccg gac ttt  gtg aaa cag ctg ggt  gat gcg gcg tct ggt                4045
Ser Thr Pro Asp Phe  Val Lys Gln Leu Gly  Asp Ala Ala Ser Gly
                         1115                    1120                    1125 cct aaa ttg ctt gct  act gca ccg act cag  gtt gtg aaa gca atc                4090
Pro Lys Leu Leu Ala  Thr Ala Pro Thr Gln  Val Val Lys Ala Ile
                         1130                    1135                    1140 aag gcg acg gtg tcg  cgt cat gag tca cct  gat cgg gcg atc cag                4135
Lys Ala Thr Val Ser  Arg His Glu Ser Pro  Asp Arg Ala Ile Gln
                         1145                    1150                    1155 gct gca cga tcg ctg  agg agg cag gag ctg  gca cgc att gcc tct                4180
Ala Ala Arg Ser Leu  Arg Arg Gln Glu Leu  Ala Arg Ile Ala Ser
                         1160                    1165                    1170 gct gat ttg ctc aac  atg ctc act gtt cag  gaa gta tgc caa agc                4225
Ala Asp Leu Leu Asn  Met Leu Thr Val Gln  Glu Val Cys Gln Ser
                         1175                    1180                    1185 ttg tca cta gtc tgg  gat gcg gtg ttg gat  gct gcc ttg gat gcg                4270
Leu Ser Leu Val Trp  Asp Ala Val Leu Asp  Ala Ala Leu Asp Ala
                         1190                    1195                    1200 gaa atc cgt gct gca  ctt aac gat cca cag  aaa cca gat cag cct                4315
Glu Ile Arg Ala Ala  Leu Asn Asp Pro Gln  Lys Pro Asp Gln Pro
                         1205                    1210                    1215 ctg gcc aat att tct  gtg atc ggc atg ggc  cgt ttg ggt gga gca                4360
Leu Ala Asn Ile Ser  Val Ile Gly Met Gly  Arg Leu Gly Gly Ala
                         1220                    1225                    1230 gaa ctt gga tac ggt  tct gat gcc gat gtg  atg ttt gta tgc gag                4405
Glu Leu Gly Tyr Gly  Ser Asp Ala Asp Val  Met Phe Val Cys Glu
                         1235                    1240                    1245 ccg gta gcc ggt gtg  gaa gag cat gag gcc  gtc aca tgg tct att                4450
Pro Val Ala Gly Val  Glu Glu His Glu Ala  Val Thr Trp Ser Ile
                         1250                    1255                    1260 gcg atc tgt gat tcc  atg cgg tcg agg ctt  gcg cag cct tcc ggt                4495
Ala Ile Cys Asp Ser  Met Arg Ser Arg Leu  Ala Gln Pro Ser Gly
                         1265                    1270                    1275 gat cca cct ttg gag  gtg gat ctg ggg ctg  cgt cct gaa ggg aga                4540
Asp Pro Pro Leu Glu  Val Asp Leu Gly Leu  Arg Pro Glu Gly Arg
                         1280                    1285                    1290 tct ggt gcg att gtg  cgc acc gtt gat tcc  tat gtg aag tac tac                4585
Ser Gly Ala Ile Val  Arg Thr Val Asp Ser  Tyr Val Lys Tyr Tyr
                         1295                    1300                    1305 gaa aag tgg ggt gaa  act tgg gag att cag  gcg ctg ctg agg gct                4630
Glu Lys Trp Gly Glu  Thr Trp Glu Ile Gln  Ala Leu Leu Arg Ala
                         1310                    1315                    1320 gcg tgg gtt gct ggt  gat cgt gag ctg ggc  att aag ttc ttg gag                4675
Ala Trp Val Ala Gly  Asp Arg Glu Leu Gly  Ile Lys Phe Leu Glu
                         1325                    1330                    1335 tcg att gat cgt ttc  cgc tac cca gtt gac  ggg gca acg cag gcg                4720
Ser Ile Asp Arg Phe  Arg Tyr Pro Val Asp  Gly Ala Thr Gln Ala
                         1340                    1345                    1350 cag ctt cgt gaa gtt  cgt cga att aag gcg  agg gtg gat aat gag                4765
Gln Leu Arg Glu Val  Arg Arg Ile Lys Ala  Arg Val Asp Asn Glu
                         1355                    1360                    1365 agg ctt ccg cgc ggg  gct gat cga aat acc  cat acc aag ctg ggt                4810
Arg Leu Pro Arg Gly  Ala Asp Arg Asn Thr  His Thr Lys Leu Gly
                         1370                    1375                    1380 cgg gga gcg tta act  gac atc gag tgg act  gtg cag ttg ttg acc                4855
```

-continued

| | | | | | | | | | | | | |
|---|---|---|---|---|---|---|---|---|---|---|---|---|
| Arg | Gly | Ala | Leu | Thr<br>1385 | Asp | Ile | Glu | Trp<br>1390 | Thr | Val | Gln | Leu | Leu | Thr<br>1395 |

```
atg atg cat gct cat  gag att ccg gag ctg  cac aat acg tcg acg          4900
Met Met His Ala His  Glu Ile Pro Glu Leu  His Asn Thr Ser Thr
            1400                    1405                1410 ttg gaa gtt ctt gaa  gtg ctg gaa aag cat  cag att att aac cct          4945
Leu Glu Val Leu Glu  Val Leu Glu Lys His  Gln Ile Ile Asn Pro
            1415                    1420                1425 gtg cag gtg cag acg  ctt cgg gaa gcg tgg  ctg acg gca acg gct          4990
Val Gln Val Gln Thr  Leu Arg Glu Ala Trp  Leu Thr Ala Thr Ala
            1430                    1435                1440 gct agg aat gcg ctt  gtg ctg gtc agg ggt  aag aga tta gat cag          5035
Ala Arg Asn Ala Leu  Val Leu Val Arg Gly  Lys Arg Leu Asp Gln
            1445                    1450                1455 tta cct act cct ggt  ccg cac ctt gcg cag  gtg gct ggt gcg tct          5080
Leu Pro Thr Pro Gly  Pro His Leu Ala Gln  Val Ala Gly Ala Ser
            1460                    1465                1470 ggt tgg gat cca aat  gag tac cag gag tat  ttg gaa aac tat ctg          5125
Gly Trp Asp Pro Asn  Glu Tyr Gln Glu Tyr  Leu Glu Asn Tyr Leu
            1475                    1480                1485 aaa gtg acc agg aag  agt cgt cag gtt gtt  gat gaa gtc ttc tgg          5170
Lys Val Thr Arg Lys  Ser Arg Gln Val Val  Asp Glu Val Phe Trp
            1490                    1495                1500 ggt gtg gac tct atg  gag caa cgt gag ttt  taggtaggtg gtgggagccc        5220
Gly Val Asp Ser Met  Glu Gln Arg Glu Phe
            1505                    1510 caaagttgcg gaaaattgtt ccaactaagg gactatatgt aggtgtggat aacctaagtt       5280 aatctttttgt gagcgtgagg atttctctga ggaatctaga cgcagattaa cttccgcttg     5340
gcagcgaccg ggataacacc gcggttgcgg ccacgcaggc tcacaaagga caccactatg      5400
acaagcatta ttgcaagcaa cagcgaccta tcggaggagc tgcgcaccca cactgcgcgg      5460
gcacatgaag aggccgagca ctcaacgttt atgaatgatc                            5500
```

<210> SEQ ID NO 2
<211> LENGTH: 446
<212> TYPE: PRT
<213> ORGANISM: Brevibacterium lactofermentum

<400> SEQUENCE: 2

```
Met Asn Ser Glu Gln Glu Phe Val Leu Ser Ala Ile Glu Glu Arg Asp
1               5                   10                  15

Ile Lys Phe Val Arg Leu Trp Phe Thr Asp Ile Leu Gly His Leu Lys
            20                  25                  30

Ser Val Val Ala Pro Ala Glu Leu Glu Ser Ala Leu Glu Glu Gly
        35                  40                  45

Ile Gly Phe Asp Gly Ser Ala Ile Glu Gly Tyr Ala Arg Ile Ser Glu
    50                  55                  60

Ala Asp Thr Ile Ala Arg Pro Asp Pro Ser Thr Phe Gln Val Leu Pro
65                  70                  75                  80

Leu Glu Ala Gly Ile Ser Lys Leu Gln Ala Ala Arg Leu Phe Cys Asp
                85                  90                  95

Val Thr Met Pro Asp Gly Gln Pro Ser Phe Ser Asp Pro Arg Gln Val
            100                 105                 110

Leu Arg Arg Gln Val Gln Leu Ala Ala Asp Glu Gly Leu Thr Cys Met
        115                 120                 125

Ile Ser Pro Glu Ile Glu Phe Tyr Leu Val Gln Ser Leu Arg Thr Asn
    130                 135                 140
```

```
Gly Leu Pro Pro Val Pro Thr Asp Asn Gly Gly Tyr Phe Asp Gln Ala
145                 150                 155                 160

Thr Phe Asn Glu Ala Pro Asn Phe Arg Arg Asn Ala Met Val Ala Leu
            165                 170                 175

Glu Glu Leu Gly Ile Pro Val Glu Phe Ser His His Glu Thr Ala Pro
            180                 185                 190

Gly Gln Gln Glu Ile Asp Leu Arg His Ala Asp Ala Leu Thr Met Ala
            195                 200                 205

Asp Asn Ile Met Thr Phe Arg Tyr Ile Met Lys Gln Val Ala Arg Asp
210                 215                 220

Gln Gly Val Gly Ala Ser Phe Met Pro Lys Pro Phe Gln Glu His Ala
225                 230                 235                 240

Gly Ser Ala Met His Thr His Met Ser Leu Phe Glu Gly Asp Thr Asn
                245                 250                 255

Ala Phe His Asp Pro Asp Asp Ser Tyr Met Leu Ser Lys Thr Ala Lys
                260                 265                 270

Gln Phe Ile Ala Gly Ile Leu His His Ala Pro Glu Phe Thr Ala Val
                275                 280                 285

Thr Asn Gln Trp Val Asn Ser Tyr Lys Arg Ile Val Tyr Gly Asn Glu
290                 295                 300

Ala Pro Thr Ala Ala Thr Trp Gly Val Ser Asn Arg Ser Ala Leu Val
305                 310                 315                 320

Arg Val Pro Thr Tyr Arg Leu Asn Lys Glu Glu Ser Arg Arg Val Glu
                325                 330                 335

Val Arg Leu Pro Asp Thr Ala Cys Asn Pro Tyr Leu Ala Phe Ser Val
                340                 345                 350

Met Leu Gly Ala Gly Leu Lys Gly Ile Lys Glu Gly Tyr Glu Leu Asp
                355                 360                 365

Glu Pro Ala Glu Asp Ile Ser Asn Leu Ser Phe Arg Glu Arg Arg
370                 375                 380

Ala Met Gly Tyr Asn Asp Leu Pro Asn Ser Leu Asp Gln Ala Leu Arg
385                 390                 395                 400

Gln Met Glu Lys Ser Glu Leu Val Ala Asp Ile Leu Gly His Val
                405                 410                 415

Phe Glu Phe Phe Leu Arg Asn Lys Trp Arg Glu Trp Arg Asp Tyr Gln
                420                 425                 430

Glu Gln Ile Thr Pro Trp Glu Leu Arg Asn Asn Leu Asp Tyr
                435                 440                 445

<210> SEQ ID NO 3
<211> LENGTH: 14
<212> TYPE: PRT
<213> ORGANISM: Brevibacterium lactofermentum

<400> SEQUENCE: 3

Ala Leu Gln Trp Lys Pro Tyr Gly Asp Pro Ile Ala Thr Arg
1               5                   10

<210> SEQ ID NO 4
<211> LENGTH: 1050
<212> TYPE: PRT
<213> ORGANISM: Brevibacterium lactofermentum

<400> SEQUENCE: 4

Arg Arg Gly Glu Ala Met Ser Gly Pro Leu Arg Ser Glu Arg Lys Val
1               5                   10                  15
```

-continued

```
Val Gly Phe Val Arg Asp Pro Leu Pro Lys Val Gly Ser Leu Ser Leu
            20                  25                  30

Lys Ser Glu His Ala Gln Ala Asp Leu Glu His Leu Gly Trp Arg Asn
        35                  40                  45

Val Glu Ser Leu Asp Leu Leu Trp Gly Leu Ser Gly Ala Gly Asp Pro
    50                  55                  60

Asp Val Ala Leu Asn Leu Leu Ile Arg Leu Tyr Gln Ala Leu Glu Ala
65                  70                  75                  80

Ile Gly Glu Asp Ala Arg Asn Glu Leu Asp Gln Glu Ile Arg Gln Asp
                85                  90                  95

Glu Glu Leu Arg Val Arg Leu Phe Ala Leu Leu Gly Ser Ser Ala
            100                 105                 110

Val Gly Asp His Leu Val Ala Asn Pro Leu Gln Trp Lys Leu Leu Lys
        115                 120                 125

Leu Asp Ala Pro Ser Arg Glu Glu Met Phe Gln Ala Leu Leu Glu Ser
    130                 135                 140

Val Lys Ala Gln Pro Ala Val Leu Glu Val Glu Asp Phe Ser Asp Ala
145                 150                 155                 160

His Asn Ile Ala Arg Asp Asp Leu Ser Thr Pro Gly Phe Tyr Thr Ala
                165                 170                 175

Ser Val Thr Gly Pro Glu Ala Glu Arg Val Leu Lys Trp Thr Tyr Arg
            180                 185                 190

Thr Leu Leu Thr Arg Ile Ala Ala His Asp Leu Ala Gly Thr Tyr Pro
        195                 200                 205

Thr Asp Met Arg Arg Lys Gly Gly Asp Pro Val Pro Phe Ser Thr Val
    210                 215                 220

Thr Met Gln Leu Ser Asp Leu Ala Asp Ala Ala Leu Thr Ala Ala Leu
225                 230                 235                 240

Ala Val Ala Ile Ala Asn Val Tyr Gly Glu Lys Pro Val Asp Ser Ala
                245                 250                 255

Leu Ser Val Ile Ala Met Gly Lys Cys Gly Ala Gln Glu Leu Asn Tyr
            260                 265                 270

Ile Ser Asp Val Asp Val Val Phe Val Ala Glu Pro Ala Asn Ser Lys
        275                 280                 285

Ser Thr Arg Thr Ala Ala Glu Leu Ile Arg Ile Gly Ser Asn Ser Phe
    290                 295                 300

Phe Glu Val Asp Ala Ala Leu Arg Pro Glu Gly Lys Ser Gly Ala Leu
305                 310                 315                 320

Val Arg Ser Leu Asp Ser His Met Ala Tyr Tyr Lys Arg Trp Ala Glu
                325                 330                 335

Thr Trp Glu Phe Gln Ala Leu Leu Lys Ala Arg Pro Met Thr Gly Asp
            340                 345                 350

Ile Asp Leu Gly Gln Ser Tyr Val Asp Ala Leu Ser Pro Leu Ile Trp
        355                 360                 365

Ala Ala Ser Gln Arg Glu Ser Phe Val Thr Asp Val Gln Ala Met Arg
    370                 375                 380

Arg Arg Val Leu Asp Asn Val Pro Glu Asp Leu Arg Asp Arg Glu Leu
385                 390                 395                 400

Lys Leu Gly Arg Gly Gly Leu Arg Asp Val Glu Phe Ala Val Gln Leu
                405                 410                 415

Leu Gln Met Val His Gly Arg Ile Asp Glu Thr Leu Arg Val Arg Ser
            420                 425                 430
```

-continued

```
Thr Val Asn Ala Leu His Val Leu Val Asp Gln Gly Tyr Val Gly Arg
            435                 440                 445

Glu Asp Gly His Asn Leu Ile Glu Ser Tyr Glu Phe Leu Arg Leu Leu
        450                 455                 460

Glu His Arg Leu Gln Leu Glu Arg Ile Lys Arg Thr His Leu Leu Pro
465                 470                 475                 480

Lys Pro Asp Asp Arg Met Asn Met Arg Trp Leu Ala Arg Ala Ser Gly
                485                 490                 495

Phe Thr Gly Ser Met Glu Gln Ser Ser Ala Lys Ala Met Glu Arg His
            500                 505                 510

Leu Arg Lys Val Arg Leu Gln Ile Gln Ser Leu His Ser Gln Leu Phe
        515                 520                 525

Tyr Arg Pro Leu Leu Asn Ser Val Val Asn Leu Ser Ala Asp Ala Ile
    530                 535                 540

Arg Leu Ser Pro Asp Ala Ala Lys Leu Gln Leu Gly Ala Leu Gly Tyr
545                 550                 555                 560

Leu His Pro Ser Arg Ala Tyr Glu His Leu Thr Ala Leu Ala Ser Gly
                565                 570                 575

Ala Ser Arg Lys Ala Lys Ile Gln Ala Met Leu Leu Pro Thr Leu Met
            580                 585                 590

Glu Trp Leu Ser Gln Thr Ala Glu Pro Asp Ala Gly Leu Leu Asn Tyr
        595                 600                 605

Arg Lys Leu Ser Asp Ala Ser Tyr Asp Arg Ser Trp Phe Leu Arg Met
    610                 615                 620

Leu Arg Asp Glu Gly Val Val Gly Gln Arg Leu Met Arg Ile Leu Gly
625                 630                 635                 640

Asn Ser Pro Tyr Ile Ser Glu Leu Ile Ile Ser Thr Pro Asp Phe Val
                645                 650                 655

Lys Gln Leu Gly Asp Ala Ala Ser Gly Pro Lys Leu Leu Ala Thr Ala
            660                 665                 670

Pro Thr Gln Val Val Lys Ala Ile Lys Ala Thr Val Ser Arg His Glu
        675                 680                 685

Ser Pro Asp Arg Ala Ile Gln Ala Ala Arg Ser Leu Arg Arg Gln Glu
    690                 695                 700

Leu Ala Arg Ile Ala Ser Ala Asp Leu Leu Asn Met Leu Thr Val Gln
705                 710                 715                 720

Glu Val Cys Gln Ser Leu Ser Leu Val Trp Asp Ala Val Leu Asp Ala
                725                 730                 735

Ala Leu Asp Ala Glu Ile Arg Ala Ala Leu Asn Asp Pro Gln Lys Pro
            740                 745                 750

Asp Gln Pro Leu Ala Asn Ile Ser Val Ile Gly Met Gly Arg Leu Gly
        755                 760                 765

Gly Ala Glu Leu Gly Tyr Gly Ser Asp Ala Asp Val Met Phe Val Cys
    770                 775                 780

Glu Pro Val Ala Gly Val Glu Glu His Glu Ala Val Thr Trp Ser Ile
785                 790                 795                 800

Ala Ile Cys Asp Ser Met Arg Ser Arg Leu Ala Gln Pro Ser Gly Asp
                805                 810                 815

Pro Pro Leu Glu Val Asp Leu Gly Leu Arg Pro Glu Gly Arg Ser Gly
            820                 825                 830

Ala Ile Val Arg Thr Val Asp Ser Tyr Val Lys Tyr Tyr Glu Lys Trp
        835                 840                 845

Gly Glu Thr Trp Glu Ile Gln Ala Leu Leu Arg Ala Ala Trp Val Ala
```

```
                850         855         860
Gly Asp Arg Glu Leu Gly Ile Lys Phe Leu Glu Ser Ile Asp Arg Phe
865                 870                 875                 880

Arg Tyr Pro Val Asp Gly Ala Thr Gln Ala Gln Leu Arg Glu Val Arg
                885                 890                 895

Arg Ile Lys Ala Arg Val Asp Asn Glu Arg Leu Pro Arg Gly Ala Asp
                900                 905                 910

Arg Asn Thr His Thr Lys Leu Gly Arg Gly Ala Leu Thr Asp Ile Glu
                915                 920                 925

Trp Thr Val Gln Leu Leu Thr Met Met His Ala His Glu Ile Pro Glu
930                 935                 940

Leu His Asn Thr Ser Thr Leu Glu Val Leu Glu Val Leu Glu Lys His
945                 950                 955                 960

Gln Ile Ile Asn Pro Val Gln Val Gln Thr Leu Arg Glu Ala Trp Leu
                965                 970                 975

Thr Ala Thr Ala Ala Arg Asn Ala Leu Val Leu Val Arg Gly Lys Arg
                980                 985                 990

Leu Asp Gln Leu Pro Thr Pro Gly Pro His Leu Ala Gln Val Ala Gly
                995                 1000                1005

Ala Ser Gly Trp Asp Pro Asn Glu Tyr Gln Glu Tyr Leu Glu Asn
        1010                1015                1020

Tyr Leu Lys Val Thr Arg Lys Ser Arg Gln Val Val Asp Glu Val
        1025                1030                1035

Phe Trp Gly Val Asp Ser Met Glu Gln Arg Glu Phe
        1040                1045                1050
```

<210> SEQ ID NO 5
<211> LENGTH: 29
<212> TYPE: DNA
<213> ORGANISM: ARTIFICIAL SEQUENCE
<220> FEATURE:
<223> OTHER INFORMATION: SYNTHETIC DNA

<400> SEQUENCE: 5
ggggtcgacg gatcgacagg taatgcatt                                     29

<210> SEQ ID NO 6
<211> LENGTH: 29
<212> TYPE: DNA
<213> ORGANISM: ARTIFICIAL SEQUENCE
<220> FEATURE:
<223> OTHER INFORMATION: SYNTHETIC DNA

<400> SEQUENCE: 6
ggggtcgacg gatccaccat gatggagga                                     29

<210> SEQ ID NO 7
<211> LENGTH: 22
<212> TYPE: DNA
<213> ORGANISM: ARTIFICIAL SEQUENCE
<220> FEATURE:
<223> OTHER INFORMATION: SYNTHETIC DNA

<400> SEQUENCE: 7
cttcccagta gcaccatacg ac                                            22

<210> SEQ ID NO 8
<211> LENGTH: 26
<212> TYPE: DNA
<213> ORGANISM: ARTIFICIAL SEQUENCE

```
<220> FEATURE:
<223> OTHER INFORMATION: SYNTHETIC DNA

<400> SEQUENCE: 8
ctggtggcag ttcgaagagg tccttg                                          26

<210> SEQ ID NO 9
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 9
ggacaaggac ctcttcgaac tgccag                                          26

<210> SEQ ID NO 10
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 10
cggcgagacc gtcgattggg aggagc                                          26

<210> SEQ ID NO 11
<211> LENGTH: 22
<212> TYPE: DNA
<213> ORGANISM: ARTIFICIAL SEQUENCE
<220> FEATURE:
<223> OTHER INFORMATION: SYNTHETIC DNA

<400> SEQUENCE: 11
gtagcacctt acgaccaaac cg                                              22

<210> SEQ ID NO 12
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 12
ggagccggtc gacgaggagc                                                 20

<210> SEQ ID NO 13
<211> LENGTH: 25
<212> TYPE: DNA
<213> ORGANISM: ARTIFICIAL SEQUENCE
<220> FEATURE:
<223> OTHER INFORMATION: SYNTHETIC DNA

<400> SEQUENCE: 13
gctagcctcg ggagctctct aggag                                           25

<210> SEQ ID NO 14
<211> LENGTH: 25
<212> TYPE: DNA
<213> ORGANISM: ARTIFICIAL SEQUENCE
<220> FEATURE:
<223> OTHER INFORMATION: SYNTHETIC DNA

<400> SEQUENCE: 14
gatctttccc agactctggc cacgc                                           25
```

<210> SEQ ID NO 15
<211> LENGTH: 17
<212> TYPE: DNA
<213> ORGANISM: ARTIFICIAL SEQUENCE
<220> FEATURE:
<223> OTHER INFORMATION: SYNTHETIC DNA

<400> SEQUENCE: 15
cagttgtggc tgatccg                                                17

<210> SEQ ID NO 16
<211> LENGTH: 18
<212> TYPE: DNA
<213> ORGANISM: ARTIFICIAL SEQUENCE
<220> FEATURE:
<223> OTHER INFORMATION: SYNTHETIC DNA

<400> SEQUENCE: 16
ctttcccaga ctctggcc                                               18

<210> SEQ ID NO 17
<211> LENGTH: 22
<212> TYPE: DNA
<213> ORGANISM: ARTIFICIAL SEQUENCE
<220> FEATURE:
<223> OTHER INFORMATION: SYNTHETIC DNA

<400> SEQUENCE: 17
cgctgctata attgaacgtg ag                                          22

<210> SEQ ID NO 18
<211> LENGTH: 44
<212> TYPE: DNA
<213> ORGANISM: ARTIFICIAL SEQUENCE
<220> FEATURE:
<223> OTHER INFORMATION: SYNTHETIC DNA

<400> SEQUENCE: 18
ctttgttgcc atatctgtgc gacgctgcta taattgaacg tgag                  44

<210> SEQ ID NO 19
<211> LENGTH: 21
<212> TYPE: DNA
<213> ORGANISM: ARTIFICIAL SEQUENCE
<220> FEATURE:
<223> OTHER INFORMATION: SYNTHETIC DNA

<400> SEQUENCE: 19
ccaccacgaa gtcggtggcg g                                           21

<210> SEQ ID NO 20
<211> LENGTH: 21
<212> TYPE: DNA
<213> ORGANISM: ARTIFICIAL SEQUENCE
<220> FEATURE:
<223> OTHER INFORMATION: SYNTHETIC DNA

<400> SEQUENCE: 20
ttggagcctc gaagcctgga a                                           21

<210> SEQ ID NO 21
<211> LENGTH: 29
<212> TYPE: DNA
<213> ORGANISM: ARTIFICIAL SEQUENCE
<220> FEATURE:
<223> OTHER INFORMATION: SYNTHETIC DNA

```
<400> SEQUENCE: 21
tggtcatatc tgtgcgacgc tgccataat                                  29

<210> SEQ ID NO 22
<211> LENGTH: 29
<212> TYPE: DNA
<213> ORGANISM: ARTIFICIAL SEQUENCE
<220> FEATURE:
<223> OTHER INFORMATION: SYNTHETIC DNA

<400> SEQUENCE: 22
tggtcatatc tgtgcgacgc tgctataat                                  29

<210> SEQ ID NO 23
<211> LENGTH: 29
<212> TYPE: DNA
<213> ORGANISM: ARTIFICIAL SEQUENCE
<220> FEATURE:
<223> OTHER INFORMATION: SYNTHETIC DNA

<400> SEQUENCE: 23
ttgccatatc tgtgcgacgc tgctataat                                  29

<210> SEQ ID NO 24
<211> LENGTH: 23
<212> TYPE: DNA
<213> ORGANISM: ARTIFICIAL SEQUENCE
<220> FEATURE:
<223> OTHER INFORMATION: SYNTHETIC DNA

<400> SEQUENCE: 24
agacctacga gtccgcctttt ttg                                       23

<210> SEQ ID NO 25
<211> LENGTH: 21
<212> TYPE: DNA
<213> ORGANISM: ARTIFICIAL SEQUENCE
<220> FEATURE:
<223> OTHER INFORMATION: SYNTHETIC DNA

<400> SEQUENCE: 25
cgatcaccag caacccacgc a                                          21
```

What is claimed is:

1. An isolated coryneform bacterium comprising a protein encoded by a polynucleotide from a coryneform bacterium, wherein said protein exhibits glutamine synthetase activity and has an amino aid sequence with at least 90% homology to the amino acid sequence of SEQ ID NO: 25, said amino acid sequence being encoded by a DNA which is obtainable from a coryneform bacterium by PCR using primers of SEQ ID NO:4 and SEQ ID NO: 5, and wherein said coryneform bacterium has a modification such that said glutamine synthetase activity is enhanced, compared to an unmodified coryneform bacterium said modification comprising a method selected from the group consisting of:

transforming said coryneform bacterium with a vector for the expression of said protein, increasing the chromosomal copy number of a polynucleotide encoding said protein, replacing the native promoter sequence for a polynucleotide encoding said protein with a stronger promoter sequence, mutating said protein to replace $Tyr_{405}$ with another amino acid such that adenylylation is suppressed, and reducing the intracellular activity of a glutamine synthetase adenylyl transferase which has at least 90% homology to the amino acid sequence of SEQ ID NO: 3, wherein the glutamine synthetase adenylyl transferase is encoded by a DNA hybridizable with a sequence containing nucleotide 2066–5200 of SEQ ID NO: 1 under stringent conditions entailing 1×SSC, 0.1% SDS at 60° C., and the DNA is obtainable from a coryneform bacterium.

2. The isolated coryneform bacterium of claim 1, wherein said bacterium belongs to the genus *Brevibacterium* or *Corynebacterium*.

3. The isolated coryneform bacterium of claim 1, wherein said modification comprises transforming said coryneform bacterium with a vector for the expression of said protein.

4. The isolated coryneform bacterium of claim 1, wherein said modification comprises increasing the chromosomal copy number of a polynucleotide encoding said protein.

5. The isolated coryneform bacterium of claim 1, wherein said modification comprises replacing the promoter for a polynucleotide encoding said protein with a strong promoter sequence.

6. The isolated coryneform bacterium of claim 5, wherein said strong promoter sequence is selected from the group consisting of a lac promoter, a trp promoter, and a trc promoter.

7. The isolated coryneform bacterium of claim 1, wherein said modification comprises mutating said protein to replace $Tyr_{405}$ with another amino acid such that adenylylation is suppressed.

8. The isolated coryneform bacterium of claim 1, wherein said glutamine synthetase adenylyl transferase has at least 90% homology to the amino acid sequence of SEQ ID NO: 3.

9. The isolated coryneform bacterium of claim 1, which is selected from the group consisting of *Corynebacterium acetoacidophilum, Corynebacterium acetoglutamicum, Corynebacterium alkanolyticum, Corynebacterium callunae, Corynebacterium glutamicum, Corynebacterium lilium, Corynebacterium melassecola, Corynebacterium thermoaminogenes, Corynebacterium herculis, Brevibacterium divaricatum, Brevibacterium flavum, Brevibacterium immariophilum, Brevibacterium laciofermentum, Brevibacterium roseum, Brevibacterium saccharolyticum, Brevibacterium thiogenitalis, Brevibacterium ammoniagenes, Brevibacterium album, Brevibacterium cerium,* and *Microbacterium ammoniaphilum.*

10. A method for producing L-glutamine, comprising cultivating the isolated coryneform bacterium of claim 1 in a culture medium for a time sufficient to produce L-glutamine; and collecting the L-glutamine produced.

* * * * *

UNITED STATES PATENT AND TRADEMARK OFFICE
CERTIFICATE OF CORRECTION

| | |
|---|---|
| PATENT NO. | : 7,262,035 B2 |
| APPLICATION NO. | : 10/062458 |
| DATED | : August 28, 2007 |
| INVENTOR(S) | : Jun Nakamura et al. |

It is certified that error appears in the above-identified patent and that said Letters Patent is hereby corrected as shown below:

Col. 47 lines 10-11 of Claim 1 should read:

--activity is enhanced compared to an unmodified coryneform bacterium, said codification--

Please delete the Sequence Listing beginning at Column 23 in it's entirety and replace with the following

```
<110>   NAKAMURA, Jun
        IZUI, Hiroshi
        MORIGUCHI, Kayo
        KAWASHIMA, Hiroki
        NAKAMATSU, TSUYOSHI <120>   Method for Producing L-Glutamine by Fermentation
        and L-Glutamine Producing Bacterium

<130>   219181US0

<140>   US 10/062,458
<141>   2001-05-30

<150>   JP 2001-28163
<151>   2001-02-05

<150>   JP 2001-162806
<151>   2001-05-30

<160>   25

<170>   PatentIn version 3.0

<210>   1
<211>   5500
<212>   DNA
<213>   Brevibacterium lactofermentum
```

UNITED STATES PATENT AND TRADEMARK OFFICE
CERTIFICATE OF CORRECTION

PATENT NO. : 7,262,035 B2
APPLICATION NO. : 10/062458
DATED : August 28, 2007
INVENTOR(S) : Jun Nakamura et al.

It is certified that error appears in the above-identified patent and that said Letters Patent is hereby corrected as shown below:

```
<220>
<221>  CDS
<222>  (659)..(1996)

<220>
<221>  CDS
<222>  (2066)..(5200)

<400>  1
gatcagtgct tcggcttctt cttcgaagtt ggtggactct gcctttttca aaagtgcggt     60
gatacgatga tgcgctttgg cctgtgccgg ggtcattggg ctggtgtctt gattgtctaa    120
ggcgtggagc tctgcgagca ttgcccagtc aggcaaggta cttagcttcg gtagctcggt    180
gagaatcttc tccagggtca tcaccggcaa gtggctagtt tcggcggcac gcgttccgtt    240
cacccacagt gtgtacatct catcggagca ggagtaagca atctcaggta gcgcgtgaaa    300
caggagtgga tcaatatcgg cggaaaactc atggcggaga tcggcgggag tccacccacg    360
aagcgcacag aaacctaggt ggctgatgat gctttcttct aaaatctgac ggtaagagtc    420
ttgtgcgtcg gtgacgttgt cggagaagtg ggagagggtc attgcggttt ccttattcgt    480
aggagagttc taatttcggt gcggttctca gtgaaccacc caagctggac acctcccacc    540
cccgtgtcat caaaaaaccg cgacatcctt gagtaactct gagaaaaact accccgatg     600 cgagtataaa agtggcaaat gcgcagtcga tgtcccatcg ctgcgtagat tagttttc     658 atg aac agc gaa cag gaa ttt gta ctc agc gcc att gaa gaa cgc gac      706
Met Asn Ser Glu Gln Glu Phe Val Leu Ser Ala Ile Glu Glu Arg Asp
1               5                   10                  15
```

UNITED STATES PATENT AND TRADEMARK OFFICE
CERTIFICATE OF CORRECTION

PATENT NO. : 7,262,035 B2
APPLICATION NO. : 10/062458
DATED : August 28, 2007
INVENTOR(S) : Jun Nakamura et al.

It is certified that error appears in the above-identified patent and that said Letters Patent is hereby corrected as shown below:

```
att aag ttt gtg cgt cta tgg ttc act gac att ctt gga cac ttg aag    754
Ile Lys Phe Val Arg Leu Trp Phe Thr Asp Ile Leu Gly His Leu Lys
        20                      25                  30 tca gtg gtt gtg gct cct gca gaa cta gag tct gcg ttg gaa gaa ggc    802
Ser Val Val Val Ala Pro Ala Glu Leu Glu Ser Ala Leu Glu Glu Gly
        35                      40                  45 atc gga ttc gat ggc tca gcc att gag ggc tac gcg cgt atc tcg gaa    850
Ile Gly Phe Asp Gly Ser Ala Ile Glu Gly Tyr Ala Arg Ile Ser Glu
    50                      55                  60 gcg gac acc att gcc cgc cca gat cca tcg aca ttc cag gtc ctc cca    898
Ala Asp Thr Ile Ala Arg Pro Asp Pro Ser Thr Phe Gln Val Leu Pro
65                      70                  75                  80 cta gaa gcg ggc atc tca aaa ctg cag gca gca cgc ctg ttt tgc gat    946
Leu Glu Ala Gly Ile Ser Lys Leu Gln Ala Ala Arg Leu Phe Cys Asp
                    85                  90                  95 gtc acg atg ccg gac gga cag cca tct ttt tct gac ccg cgc caa gtg    994
Val Thr Met Pro Asp Gly Gln Pro Ser Phe Ser Asp Pro Arg Gln Val
            100                 105                 110 ctg cgc agg cag gtc caa cta gct gca gat gaa ggc ttg acc tgc atg   1042
Leu Arg Arg Gln Val Gln Leu Ala Ala Asp Glu Gly Leu Thr Cys Met
            115                 120                 125 gga ctg cca cct gtg ccc act gac aac ggc gga tat ttc gac caa gcc   1138
Gly Leu Pro Pro Val Pro Thr Asp Asn Gly Gly Tyr Phe Asp Gln Ala
145                 150                 155                 160
```

UNITED STATES PATENT AND TRADEMARK OFFICE
CERTIFICATE OF CORRECTION

PATENT NO. : 7,262,035 B2  
APPLICATION NO. : 10/062458  
DATED : August 28, 2007  
INVENTOR(S) : Jun Nakamura et al.

Page 4 of 31

It is certified that error appears in the above-identified patent and that said Letters Patent is hereby corrected as shown below:

```
      aca ttc aat gag gcg ccg aat ttc cgt cga aac gcg atg gta gcg ctg
 1186
      Thr Phe Asn Glu Ala Pro Asn Phe Arg Arg Asn Ala Met Val Ala Leu
                      165             170             175 gag gaa ctc ggc atc cct gtc gag ttc tcc cac cat gaa act gca cct   1234
      Glu Glu Leu Gly Ile Pro Val Glu Phe Ser His His Glu Thr Ala Pro
                      180             185             190 ggc cag caa gaa atc gat tta cgc cat gcg gat gcg ctc acc atg gcc   1282
      Gly Gln Gln Glu Ile Asp Leu Arg His Ala Asp Ala Leu Thr Met Ala
                  195             200             205 gac aac atc atg acc ttc cgc tac atc atg aaa cag gtg gca agg gac   1330
      Asp Asn Ile Met Thr Phe Arg Tyr Ile Met Lys Gln Val Ala Arg Asp
              210             215             220 caa ggc gtt ggg gca tca ttt atg ccc aag cca ttc caa gaa cat gca   1378
      Gln Gly Val Gly Ala Ser Phe Met Pro Lys Pro Phe Gln Glu His Ala
      225             230             235             240 ggc tcc gcc atg cac acg cac atg tcc tta ttt gag ggc gat acc aac   1426
      Gly Ser Ala Met His Thr His Met Ser Leu Phe Glu Gly Asp Thr Asn
                      245             250             255 gcg ttc cac gat cca gac gat tct tac atg ctg tcc aaa acc gca aaa   1474
      Ala Phe His Asp Pro Asp Asp Ser Tyr Met Leu Ser Lys Thr Ala Lys
                      260             265             270 cag ttc atc gct gga atc ttg cat cac gct cca gaa ttc acc gct gtg   1522
      Gln Phe Ile Ala Gly Ile Leu His His Ala Pro Glu Phe Thr Ala Val
                  275             280             285
```

UNITED STATES PATENT AND TRADEMARK OFFICE
CERTIFICATE OF CORRECTION

PATENT NO. : 7,262,035 B2
APPLICATION NO. : 10/062458
DATED : August 28, 2007
INVENTOR(S) : Jun Nakamura et al.

It is certified that error appears in the above-identified patent and that said Letters Patent is hereby corrected as shown below:

```
acc aac cag tgg gtc aat tcc tac aaa cgc atc gtg tac gga aac gaa    1570
Thr Asn Gln Trp Val Asn Ser Tyr Lys Arg Ile Val Tyr Gly Asn Glu
    290                 295                 300 gct cca act gcg gca acc tgg ggt gta tct aat cgt tct gcg ctg gtt    1618
Ala Pro Thr Ala Ala Thr Trp Gly Val Ser Asn Arg Ser Ala Leu Val
305                 310                 315                 320 cgt gtt cct acc tac cgt ttg aat aag gag gag tcg cgc cgg gtg gag    1666
Arg Val Pro Thr Tyr Arg Leu Asn Lys Glu Glu Ser Arg Arg Val Glu
                325                 330                 335 gtg cgt ctt cct gat acc gct tgt aac cca tat ttg gcg ttt tca gtg    1714
Val Arg Leu Pro Asp Thr Ala Cys Asn Pro Tyr Leu Ala Phe Ser Val
            340                 345                 350 atg ctc ggc gct ggt ttg aaa ggt att aaa gaa ggt tat gag ctc gac    1762
Met Leu Gly Ala Gly Leu Lys Gly Ile Lys Glu Gly Tyr Glu Leu Asp
                355                 360                 365 gag cca gct gag gac gat atc tcc aac ttg agc ttc cgg gaa cgt cgc    1810
Glu Pro Ala Glu Asp Asp Ile Ser Asn Leu Ser Phe Arg Glu Arg Arg
    370                 375                 380 gcc atg ggc tac aac gat ctg cca aac agc ctt gat cag gca ctg cgc    1858
Ala Met Gly Tyr Asn Asp Leu Pro Asn Ser Leu Asp Gln Ala Leu Arg
385                 390                 395                 400 caa atg gaa aag tca gag ctt gtt gct gac atc ctc ggt gag cac gtt    1906
Gln Met Glu Lys Ser Glu Leu Val Ala Asp Ile Leu Gly Glu His Val
                405                 410                 415 ttt gag ttt ttc ttg cgc aat aag tgg cgt gaa tgg cgt gac tac caa    1954
Phe Glu Phe Phe Leu Arg Asn Lys Trp Arg Glu Trp Arg Asp Tyr Gln
            420                 425                 430
```

UNITED STATES PATENT AND TRADEMARK OFFICE
CERTIFICATE OF CORRECTION

PATENT NO. : 7,262,035 B2
APPLICATION NO. : 10/062458
DATED : August 28, 2007
INVENTOR(S) : Jun Nakamura et al.

It is certified that error appears in the above-identified patent and that said Letters Patent is hereby corrected as shown below:

```
     gag cag atc act ccg tgg gag ctc cga aac aat ctt gat tac            1996
     Glu Gln Ile Thr Pro Trp Glu Leu Arg Asn Asn Leu Asp Tyr
             435                 440                 445 tagacttttg cactccaatg gaaaccctac ggcgacccaa ttgcgacccg ataaaggagg  2056 ggagaagct atg tca gga ccg tta aga agt gaa cgt aaa gtc gtt ggc ttt  2107
               Met Ser Gly Pro Leu Arg Ser Glu Arg Lys Val Val Gly Phe
                           450                 455                 460 gtc aga gac cca ctg cca aaa gtt ggt tct tta tcg ctg aaa tct gag    2155
     Val Arg Asp Pro Leu Pro Lys Val Gly Ser Leu Ser Leu Lys Ser Glu
                     465                 470                 475 cat gcc caa gca gat cta gag cat ttg ggt tgg cgc aat gtt gag tct    2203
     His Ala Gln Ala Asp Leu Glu His Leu Gly Trp Arg Asn Val Glu Ser
                     480                 485                 490 ttg gat ttg ttg tgg ggc ttg tca ggt gca ggc gat ccc gat gtc gcg    2251
     Leu Asp Leu Leu Trp Gly Leu Ser Gly Ala Gly Asp Pro Asp Val Ala
                     495                 500                 505 ctg aac ctt ctt att cgg ctg tat cag gca ctt gaa gca atc ggc gag    2299
     Leu Asn Leu Leu Ile Arg Leu Tyr Gln Ala Leu Glu Ala Ile Gly Glu
                     510                 515                 520 gat gct cga aac gag ctt gat caa gag att cgc cag gat gaa gaa cta    2347
     Asp Ala Arg Asn Glu Leu Asp Gln Glu Ile Arg Gln Asp Glu Glu Leu
     525                 530                 535                 540 cga gtc cgc ctt ttt gca ttg ttg ggt ggt tcc tcg gct gtc ggt gat    2395
     Arg Val Arg Leu Phe Ala Leu Leu Gly Gly Ser Ser Ala Val Gly Asp
                     545                 550                 555
```

UNITED STATES PATENT AND TRADEMARK OFFICE
CERTIFICATE OF CORRECTION

PATENT NO. : 7,262,035 B2
APPLICATION NO. : 10/062458
DATED : August 28, 2007
INVENTOR(S) : Jun Nakamura et al.

It is certified that error appears in the above-identified patent and that said Letters Patent is hereby corrected as shown below:

```
cac ttg gtc gcc aat cct ttg cag tgg aaa ctc tta aaa ctt gat gcg      2443
His Leu Val Ala Asn Pro Leu Gln Trp Lys Leu Leu Lys Leu Asp Ala
            560             565             570 cca tcg agg gaa gag atg ttt cag gcg ctg ctg gaa tct gtg aaa gct      2491
Pro Ser Arg Glu Glu Met Phe Gln Ala Leu Leu Glu Ser Val Lys Ala
        575             580             585 cag cct gct gtg ctt gag gtt gag gat ttc agc gat gca cac aac att      2539
Gln Pro Ala Val Leu Glu Val Glu Asp Phe Ser Asp Ala His Asn Ile
        590             595             600 gcc cga gac gat ttg agc acg cct ggt ttt tac acg gct agt gtt acc      2587
Ala Arg Asp Asp Leu Ser Thr Pro Gly Phe Tyr Thr Ala Ser Val Thr
605             610             615             620 ggg cct gaa gca gag cga gtc ttg aaa tgg act tat cgc acg ttg ctg      2635
Gly Pro Glu Ala Glu Arg Val Leu Lys Trp Thr Tyr Arg Thr Leu Leu
            625             630             635 acc cgg att gct gcg cat gat tta gcg ggt acc tat ccc acc gac atg      2683
Thr Arg Ile Ala Ala His Asp Leu Ala Gly Thr Tyr Pro Thr Asp Met
            640             645             650 cgg aga aaa ggt ggc gat cct gtt ccg ttt agc aca gtg acc atg cag      2731
Arg Arg Lys Gly Gly Asp Pro Val Pro Phe Ser Thr Val Thr Met Gln
        655             660             665 ctc agc gac cta gct gat gct gct ttg act gct gct tta gct gtg gca      2779
Leu Ser Asp Leu Ala Asp Ala Ala Leu Thr Ala Ala Leu Ala Val Ala
        670             675             680 att gcc aat gtt tat ggt gaa aag ccg gtt gat tca gct tta tct gtc      2827
Ile Ala Asn Val Tyr Gly Glu Lys Pro Val Asp Ser Ala Leu Ser Val
685             690             695             700
```

UNITED STATES PATENT AND TRADEMARK OFFICE
CERTIFICATE OF CORRECTION

PATENT NO.        : 7,262,035 B2                              Page 8 of 31
APPLICATION NO.   : 10/062458
DATED             : August 28, 2007
INVENTOR(S)       : Jun Nakamura et al.

It is certified that error appears in the above-identified patent and that said Letters Patent is hereby corrected as shown below:

```
        atc gcg atg ggc aaa tgt ggc gcg cag gaa ttg aac tac att tca gat      2875
        Ile Ala Met Gly Lys Cys Gly Ala Gln Glu Leu Asn Tyr Ile Ser Asp
                        705             710             715 gtg gac gtg gtg ttt gtt gca gag ccg gca aac tct aaa tca aca cgc      2923
        Val Asp Val Val Phe Val Ala Glu Pro Ala Asn Ser Lys Ser Thr Arg
                        720             725             730 acc gca gca gag ctc att cgc atc ggt agc aac tcg ttc ttt gag gtg      2971
        Thr Ala Ala Glu Leu Ile Arg Ile Gly Ser Asn Ser Phe Phe Glu Val
                        735             740             745 gat gca gca ctt cgc cca gaa ggt aaa agt ggc gct ctt gtg cgc tct      3019
        Asp Ala Ala Leu Arg Pro Glu Gly Lys Ser Gly Ala Leu Val Arg Ser
                        750             755             760 ttg gat tcc cat atg gcg tat tac aag cgc tgg gcg gaa acc tgg gaa      3067
        Leu Asp Ser His Met Ala Tyr Tyr Lys Arg Trp Ala Glu Thr Trp Glu
        765             770             775             780 ttt cag gca ctg ctg aaa gct cgt ccc atg acg ggt gat att gac ctt      3115
        Phe Gln Ala Leu Leu Lys Ala Arg Pro Met Thr Gly Asp Ile Asp Leu
                        785             790             795 ggg cag tcc tat gtg gat gct ctt tca ccg ttg att tgg gcg gct agc      3163
        Gly Gln Ser Tyr Val Asp Ala Leu Ser Pro Leu Ile Trp Ala Ala Ser
                        800             805             810 cag cgg gaa tca ttt gtc aca gat gtc caa gct atg cgc cgt cga gtg      3211
        Gln Arg Glu Ser Phe Val Thr Asp Val Gln Ala Met Arg Arg Arg Val
                        815             820             825 ttg gac aat gtt ccg gaa gac ttg cgt gat cgt gag ctg aag ctt ggt      3259
        Leu Asp Asn Val Pro Glu Asp Leu Arg Asp Arg Glu Leu Lys Leu Gly
                        830             835             840
```

UNITED STATES PATENT AND TRADEMARK OFFICE
CERTIFICATE OF CORRECTION

PATENT NO. : 7,262,035 B2
APPLICATION NO. : 10/062458
DATED : August 28, 2007
INVENTOR(S) : Jun Nakamura et al.

It is certified that error appears in the above-identified patent and that said Letters Patent is hereby corrected as shown below:

```
cgc ggt ggt ttg agg gat gtg gag ttt gct gtc cag ctc ctt cag atg     3307
Arg Gly Gly Leu Arg Asp Val Glu Phe Ala Val Gln Leu Leu Gln Met
845             850             855             860 gtg cat ggt cgc att gat gag acg ttg cgg gtt cgg tca acg gta aat     3355
Val His Gly Arg Ile Asp Glu Thr Leu Arg Val Arg Ser Thr Val Asn
                865             870             875 gct ttg cat gtg ttg gtt gat cag gga tat gtg ggt cgt gaa gac ggg     3403
Ala Leu His Val Leu Val Asp Gln Gly Tyr Val Gly Arg Glu Asp Gly
            880             885             890 cat aat ctc att gag tcg tat gag ttt ttg cgc ctg ttg gag cat cgc     3451
His Asn Leu Ile Glu Ser Tyr Glu Phe Leu Arg Leu Leu Glu His Arg
        895             900             905 ctt caa ttg gag cgg atc aag cgc act cac ttg tta ccg aaa cct gat     3499
Leu Gln Leu Glu Arg Ile Lys Arg Thr His Leu Leu Pro Lys Pro Asp
    910             915             920 gac cga atg aat atg cgc tgg ttg gcg cgc gct tct ggg ttt act ggt     3547
Asp Arg Met Asn Met Arg Trp Leu Ala Arg Ala Ser Gly Phe Thr Gly
925             930             935             940 tcg atg gag caa agt tcg gcc aaa gct atg gaa cgg cat ttg cgt aag     3595
Ser Met Glu Gln Ser Ser Ala Lys Ala Met Glu Arg His Leu Arg Lys
            945             950             955 gtt cgt ttg cag att cag tcg ttg cat agt cag ctg ttt tat cgg cca     3643
Val Arg Leu Gln Ile Gln Ser Leu His Ser Gln Leu Phe Tyr Arg Pro
        960             965             970 ctg ctg aac tct gtg gtc aac ttg agc gcg gat gcc atc aga ttg tct     3691
Leu Leu Asn Ser Val Val Asn Leu Ser Ala Asp Ala Ile Arg Leu Ser
    975             980             985
```

UNITED STATES PATENT AND TRADEMARK OFFICE
CERTIFICATE OF CORRECTION

PATENT NO. : 7,262,035 B2
APPLICATION NO. : 10/062458
DATED : August 28, 2007
INVENTOR(S) : Jun Nakamura et al.

It is certified that error appears in the above-identified patent and that said Letters Patent is hereby corrected as shown below:

```
        ccg gat gct gca aag cta caa ttg ggg gca ttg gga  tac ctg cat cca      3739
        Pro Asp Ala Ala Lys Leu Gln Leu Gly Ala Leu Gly  Tyr Leu His Pro
            990                 995                 1000 tca cgt gct tat gaa cac ctg act gct ctt gca tca gga gct agc           3784
        Ser Arg Ala Tyr Glu His Leu Thr Ala Leu Ala Ser Gly Ala Ser
        1005                1010                1015 cgt aaa gcc aag att cag gcg atg ttg ctg ccc acg ttg atg gag           3829
        Arg Lys Ala Lys Ile Gln Ala Met Leu Leu Pro Thr Leu Met Glu
        1020                1025                1030 tgg ctg tct caa aca gct gaa cca gat gcg gga ttg ctg aat tac           3874
        Trp Leu Ser Gln Thr Ala Glu Pro Asp Ala Gly Leu Leu Asn Tyr
        1035                1040                1045 cgc aag ctt tct gat gct tcc tat gat cgc agc tgg ttt ttg cgc           3919
        Arg Lys Leu Ser Asp Ala Ser Tyr Asp Arg Ser Trp Phe Leu Arg
        1050                1055                1060 atg ctg cgt gat gag ggc gta gtg ggg cag cgg ttg atg cgt att           3964
        Met Leu Arg Asp Glu Gly Val Val Gly Gln Arg Leu Met Arg Ile
        1065                1070                1075 ttg gga aat tct ccc tat att tct gaa ctg att atc tcc act ccg           4009
        Leu Gly Asn Ser Pro Tyr Ile Ser Glu Leu Ile Ile Ser Thr Pro
        1080                1085                1090 gac ttt gtg aaa cag ctg ggt gat gcg gcg tct ggt cct aaa ttg           4054
        Asp Phe Val Lys Gln Leu Gly Asp Ala Ala Ser Gly Pro Lys Leu
        1095                1100                1105 ctt gct act gca ccg act cag gtt gtg aaa gca atc aag gcg acg           4099
        Leu Ala Thr Ala Pro Thr Gln Val Val Lys Ala Ile Lys Ala Thr
        1110                1115                1120 gtg tcg cgt cat gag tca cct gat cgg gcg atc cag gct gca cga           4144
        Val Ser Arg His Glu Ser Pro Asp Arg Ala Ile Gln Ala Ala Arg
        1125                1130                1135
```

UNITED STATES PATENT AND TRADEMARK OFFICE
CERTIFICATE OF CORRECTION

PATENT NO. : 7,262,035 B2  Page 11 of 31
APPLICATION NO. : 10/062458
DATED : August 28, 2007
INVENTOR(S) : Jun Nakamura et al.

It is certified that error appears in the above-identified patent and that said Letters Patent is hereby corrected as shown below:

```
      tcg ctg agg agg cag gag ctg gca cgc att gcc tct gct gat ttg       4189
      Ser Leu Arg Arg Gln Glu Leu Ala Arg Ile Ala Ser Ala Asp Leu
      1140            1145            1150 ctc aac atg ctc act gtt cag gaa gta tgc caa agc ttg tca cta       4234
      Leu Asn Met Leu Thr Val Gln Glu Val Cys Gln Ser Leu Ser Leu
      1155            1160            1165 gtc tgg gat gcg gtg ttg gat gct gcc ttg gat gcg gaa atc cgt       4279
      Val Trp Asp Ala Val Leu Asp Ala Ala Leu Asp Ala Glu Ile Arg
      1170            1175            1180 gct gca ctt aac gat cca cag aaa cca gat cag cct ctg gcc aat       4324
      Ala Ala Leu Asn Asp Pro Gln Lys Pro Asp Gln Pro Leu Ala Asn
      1185            1190            1195 att tct gtg atc ggc atg ggc cgt ttg ggt gga gca gaa ctt gga       4369
      Ile Ser Val Ile Gly Met Gly Arg Leu Gly Gly Ala Glu Leu Gly
      1200            1205            1210 tac ggt tct gat gcc gat gtg atg ttt gta tgc gag ccg gta gcc       4414
      Tyr Gly Ser Asp Ala Asp Val Met Phe Val Cys Glu Pro Val Ala
      1215            1220            1225 ggt gtg gaa gag cat gag gcc gtc aca tgg tct att gcg atc tgt       4459
      Gly Val Glu Glu His Glu Ala Val Thr Trp Ser Ile Ala Ile Cys
      1230            1235            1240 gat tcc atg cgg tcg agg ctt gcg cag cct tcc ggt gat cca cct       4504
      Asp Ser Met Arg Ser Arg Leu Ala Gln Pro Ser Gly Asp Pro Pro
      1245            1250            1255 ttg gag gtg gat ctg ggg ctg cgt cct gaa ggg aga tct ggt gcg       4549
      Leu Glu Val Asp Leu Gly Leu Arg Pro Glu Gly Arg Ser Gly Ala
      1260            1265            1270 att gtg cgc acc gtt gat tcc tat gtg aag tac tac gaa aag tgg       4594
      Ile Val Arg Thr Val Asp Ser Tyr Val Lys Tyr Tyr Glu Lys Trp
      1275            1280            1285
```

UNITED STATES PATENT AND TRADEMARK OFFICE
CERTIFICATE OF CORRECTION

PATENT NO. : 7,262,035 B2
APPLICATION NO. : 10/062458
DATED : August 28, 2007
INVENTOR(S) : Jun Nakamura et al.

It is certified that error appears in the above-identified patent and that said Letters Patent is hereby corrected as shown below:

```
ggt gaa act tgg gag att cag gcg ctg ctg agg gct gcg tgg gtt     4639
Gly Glu Thr Trp Glu Ile Gln Ala Leu Leu Arg Ala Ala Trp Val
1290                1295                1300 gct ggt gat cgt gag ctg ggc att aag ttc ttg gag tcg att gat     4684
Ala Gly Asp Arg Glu Leu Gly Ile Lys Phe Leu Glu Ser Ile Asp
1305                1310                1315 cgt ttc cgc tac cca gtt gac ggg gca acg cag gcg cag ctt cgt     4729
Arg Phe Arg Tyr Pro Val Asp Gly Ala Thr Gln Ala Gln Leu Arg
1320                1325                1330 gaa gtt cgt cga att aag gcg agg gtg gat aat gag agg ctt ccg     4774
Glu Val Arg Arg Ile Lys Ala Arg Val Asp Asn Glu Arg Leu Pro
1335                1340                1345 cgc ggg gct gat cga aat acc cat acc aag ctg ggt cgg gga gcg     4819
Arg Gly Ala Asp Arg Asn Thr His Thr Lys Leu Gly Arg Gly Ala
1350                1355                1360 tta act gac atc gag tgg act gtg cag ttg ttg acc atg atg cat     4864
Leu Thr Asp Ile Glu Trp Thr Val Gln Leu Leu Thr Met Met His
1365                1370                1375 gct cat gag att ccg gag ctg cac aat acg tcg acg ttg gaa gtt     4909
Ala His Glu Ile Pro Glu Leu His Asn Thr Ser Thr Leu Glu Val
1380                1385                1390 ctt gaa gtg ctg gaa aag cat cag att att aac cct gtg cag gtg     4954
Leu Glu Val Leu Glu Lys His Gln Ile Ile Asn Pro Val Gln Val
1395                1400                1405 cag acg ctt cgg gaa gcg tgg ctg acg gca acg gct gct agg aat     4999
Gln Thr Leu Arg Glu Ala Trp Leu Thr Ala Thr Ala Ala Arg Asn
1410                1415                1420 gcg ctt gtg ctg gtc agg ggt aag aga tta gat cag tta cct act     5044
Ala Leu Val Leu Val Arg Gly Lys Arg Leu Asp Gln Leu Pro Thr
1425                1430                1435
```

UNITED STATES PATENT AND TRADEMARK OFFICE
CERTIFICATE OF CORRECTION

PATENT NO. : 7,262,035 B2  Page 13 of 31
APPLICATION NO. : 10/062458
DATED : August 28, 2007
INVENTOR(S) : Jun Nakamura et al.

It is certified that error appears in the above-identified patent and that said Letters Patent is hereby corrected as shown below:

```
cct  ggt  ccg  cac  ctt  gcg  cag  gtg  gct  ggt  gcg  tct  ggt  tgg  gat        5089
Pro  Gly  Pro  His  Leu  Ala  Gln  Val  Ala  Gly  Ala  Ser  Gly  Trp  Asp
1440                     1445                1450 cca  aat  gag  tac  cag  gag  tat  ttg  gaa  aac  tat  ctg  aaa  gtg  acc        5134
Pro  Asn  Glu  Tyr  Gln  Glu  Tyr  Leu  Glu  Asn  Tyr  Leu  Lys  Val  Thr
1455                     1460                1465 agg  aag  agt  cgt  cag  gtt  gtt  gat  gaa  gtc  ttc  tgg  ggt  gtg  gac        5179
Arg  Lys  Ser  Arg  Gln  Val  Val  Asp  Glu  Val  Phe  Trp  Gly  Val  Asp
1470                     1475                1480 tct  atg  gag  caa  cgt  gag  ttt  taggtaggtg  gtgggagccc  caaagttgcg            5230
Ser  Met  Glu  Gln  Arg  Glu  Phe
1485                     1490 gaaattgtt  ccaactaagg  gactatatgt  aggtgtggat  aacctaagtt  aatcttttgt            5290
gagcgtgagg  atttctctga  ggaatctaga  cgcagattaa  cttccgcttg  gcagcgaccg            5350
ggataacacc  gcggttgcgg  ccacgcaggc  tcacaaagga  caccactatg  acaagcatta           5410
ttgcaagcaa  cagcgaccta  tcggaggagc  tgcgcaccca  cactgcgcgg  gcacatgaag           5470
aggccgagca  ctcaacgttt  atgaatgatc                                               5500
```

<210> 2
<211> 446
<212> PRT
<213> Brevibacterium lactofermentum

<400> 2

```
Met  Asn  Ser  Glu  Gln  Glu  Phe  Val  Leu  Ser  Ala  Ile  Glu  Glu  Arg  Asp
1                 5                       10                      15

Ile  Lys  Phe  Val  Arg  Leu  Trp  Phe  Thr  Asp  Ile  Leu  Gly  His  Leu  Lys
             20                      25                      30
```

UNITED STATES PATENT AND TRADEMARK OFFICE
CERTIFICATE OF CORRECTION

PATENT NO. : 7,262,035 B2
APPLICATION NO. : 10/062458
DATED : August 28, 2007
INVENTOR(S) : Jun Nakamura et al.

It is certified that error appears in the above-identified patent and that said Letters Patent is hereby corrected as shown below:

```
Ser Val Val Val Ala Pro Ala Glu Leu Glu Ser Ala Leu Glu Glu Gly
        35                  40                  45

Ile Gly Phe Asp Gly Ser Ala Ile Glu Gly Tyr Ala Arg Ile Ser Glu
    50                  55                  60

Ala Asp Thr Ile Ala Arg Pro Asp Pro Ser Thr Phe Gln Val Leu Pro
65                  70                  75                  80

Leu Glu Ala Gly Ile Ser Lys Leu Gln Ala Ala Arg Leu Phe Cys Asp
                85                  90                  95

Val Thr Met Pro Asp Gly Gln Pro Ser Phe Ser Asp Pro Arg Gln Val
            100                 105                 110

Leu Arg Arg Gln Val Gln Leu Ala Ala Asp Glu Gly Leu Thr Cys Met
            115                 120                 125

Ile Ser Pro Glu Ile Glu Phe Tyr Leu Val Gln Ser Leu Arg Thr Asn
        130                 135                 140

Gly Leu Pro Pro Val Pro Thr Asp Asn Gly Gly Tyr Phe Asp Gln Ala
145                 150                 155                 160

Thr Phe Asn Glu Ala Pro Asn Phe Arg Arg Asn Ala Met Val Ala Leu
                165                 170                 175

Glu Glu Leu Gly Ile Pro Val Glu Phe Ser His His Glu Thr Ala Pro
                180                 185                 190
```

UNITED STATES PATENT AND TRADEMARK OFFICE
CERTIFICATE OF CORRECTION

PATENT NO. : 7,262,035 B2
APPLICATION NO. : 10/062458
DATED : August 28, 2007
INVENTOR(S) : Jun Nakamura et al.

It is certified that error appears in the above-identified patent and that said Letters Patent is hereby corrected as shown below:

```
Gly Gln Gln Glu Ile Asp Leu Arg His Ala Asp Ala Leu Thr Met Ala
        195             200             205

Asp Asn Ile Met Thr Phe Arg Tyr Ile Met Lys Gln Val Ala Arg Asp
    210             215             220

Gln Gly Val Gly Ala Ser Phe Met Pro Lys Pro Phe Gln Glu His Ala
225             230             235                         240

Gly Ser Ala Met His Thr His Met Ser Leu Phe Glu Gly Asp Thr Asn
            245             250             255

Ala Phe His Asp Pro Asp Asp Ser Tyr Met Leu Ser Lys Thr Ala Lys
            260             265             270

Gln Phe Ile Ala Gly Ile Leu His His Ala Pro Glu Phe Thr Ala Val
        275             280             285

Thr Asn Gln Trp Val Asn Ser Tyr Lys Arg Ile Val Tyr Gly Asn Glu
    290             295             300

Ala Pro Thr Ala Ala Thr Trp Gly Val Ser Asn Arg Ser Ala Leu Val
305             310             315                         320

Arg Val Pro Thr Tyr Arg Leu Asn Lys Glu Glu Ser Arg Arg Val Glu
            325             330             335
```

UNITED STATES PATENT AND TRADEMARK OFFICE
CERTIFICATE OF CORRECTION

PATENT NO.        : 7,262,035 B2
APPLICATION NO.   : 10/062458
DATED             : August 28, 2007
INVENTOR(S)       : Jun Nakamura et al.

It is certified that error appears in the above-identified patent and that said Letters Patent is hereby corrected as shown below:

```
Val Arg Leu Pro Asp Thr Ala Cys Asn Pro Tyr Leu Ala Phe Ser Val
            340             345             350

Met Leu Gly Ala Gly Leu Lys Gly Ile Lys Glu Gly Tyr Glu Leu Asp
            355             360             365

Glu Pro Ala Glu Asp Asp Ile Ser Asn Leu Ser Phe Arg Glu Arg Arg
            370             375             380

Ala Met Gly Tyr Asn Asp Leu Pro Asn Ser Leu Asp Gln Ala Leu Arg
385             390             395             400

Gln Met Glu Lys Ser Glu Leu Val Ala Asp Ile Leu Gly Glu His Val
            405             410             415

Phe Glu Phe Phe Leu Arg Asn Lys Trp Arg Glu Trp Arg Asp Tyr Gln
            420             425             430

Glu Gln Ile Thr Pro Trp Glu Leu Arg Asn Asn Leu Asp Tyr
            435             440             445

<210> 3
<211> 1045
<212> PRT
<213> Brevibacterium lactofermentum

<400> 3

Met Ser Gly Pro Leu Arg Ser Glu Arg Lys Val Val Gly Phe Val Arg
1               5               10              15

Asp Pro Leu Pro Lys Val Gly Ser Leu Ser Leu Lys Ser Glu His Ala
            20              25              30
```

UNITED STATES PATENT AND TRADEMARK OFFICE
CERTIFICATE OF CORRECTION

PATENT NO. : 7,262,035 B2
APPLICATION NO. : 10/062458
DATED : August 28, 2007
INVENTOR(S) : Jun Nakamura et al.

It is certified that error appears in the above-identified patent and that said Letters Patent is hereby corrected as shown below:

```
Gln Ala Asp Leu Glu His Leu Gly Trp Arg Asn Val Glu Ser Leu Asp
        35                  40                  45

Leu Leu Trp Gly Leu Ser Gly Ala Gly Asp Pro Asp Val Ala Leu Asn
    50                  55                  60

Leu Leu Ile Arg Leu Tyr Gln Ala Leu Glu Ala Ile Gly Glu Asp Ala
65              70                  75                      80

Arg Asn Glu Leu Asp Gln Glu Ile Arg Gln Asp Glu Glu Leu Arg Val
            85                  90                  95

Arg Leu Phe Ala Leu Leu Gly Gly Ser Ser Ala Val Gly Asp His Leu
            100             105                 110

Val Ala Asn Pro Leu Gln Trp Lys Leu Leu Lys Leu Asp Ala Pro Ser
            115                 120                 125

Arg Glu Glu Met Phe Gln Ala Leu Leu Glu Ser Val Lys Ala Gln Pro
        130                 135                 140

Ala Val Leu Glu Val Glu Asp Phe Ser Asp Ala His Asn Ile Ala Arg
145                 150                 155                 160

Asp Asp Leu Ser Thr Pro Gly Phe Tyr Thr Ala Ser Val Thr Gly Pro
                165                 170                 175

Glu Ala Glu Arg Val Leu Lys Trp Thr Tyr Arg Thr Leu Leu Thr Arg
            180                 185                 190
```

UNITED STATES PATENT AND TRADEMARK OFFICE
CERTIFICATE OF CORRECTION

PATENT NO. : 7,262,035 B2
APPLICATION NO. : 10/062458
DATED : August 28, 2007
INVENTOR(S) : Jun Nakamura et al.

It is certified that error appears in the above-identified patent and that said Letters Patent is hereby corrected as shown below:

```
Ile Ala Ala His Asp Leu Ala Gly Thr Tyr Pro Thr Asp Met Arg Arg
    195             200             205

Lys Gly Gly Asp Pro Val Pro Phe Ser Thr Val Thr Met Gln Leu Ser
    210             215             220

Asp Leu Ala Asp Ala Ala Leu Thr Ala Ala Leu Ala Val Ala Ile Ala
225             230             235             240

Asn Val Tyr Gly Glu Lys Pro Val Asp Ser Ala Leu Ser Val Ile Ala
            245             250             255

Met Gly Lys Cys Gly Ala Gln Glu Leu Asn Tyr Ile Ser Asp Val Asp
            260             265             270

Val Val Phe Val Ala Glu Pro Ala Asn Ser Lys Ser Thr Arg Thr Ala
        275             280             285

Ala Glu Leu Ile Arg Ile Gly Ser Asn Ser Phe Phe Glu Val Asp Ala
    290             295             300

Ala Leu Arg Pro Glu Gly Lys Ser Gly Ala Leu Val Arg Ser Leu Asp
305             310             315             320

Ser His Met Ala Tyr Tyr Lys Arg Trp Ala Glu Thr Trp Glu Phe Gln
            325             330             335
```

UNITED STATES PATENT AND TRADEMARK OFFICE
CERTIFICATE OF CORRECTION

PATENT NO. : 7,262,035 B2
APPLICATION NO. : 10/062458
DATED : August 28, 2007
INVENTOR(S) : Jun Nakamura et al.

It is certified that error appears in the above-identified patent and that said Letters Patent is hereby corrected as shown below:

```
Ala Leu Leu Lys Ala Arg Pro Met Thr Gly Asp Ile Asp Leu Gly Gln
            340             345             350

Ser Tyr Val Asp Ala Leu Ser Pro Leu Ile Trp Ala Ala Ser Gln Arg
            355             360             365

Glu Ser Phe Val Thr Asp Val Gln Ala Met Arg Arg Arg Val Leu Asp
            370             375             380

Asn Val Pro Glu Asp Leu Arg Asp Arg Glu Leu Lys Leu Gly Arg Gly
385             390             395             400

Gly Leu Arg Asp Val Glu Phe Ala Val Gln Leu Leu Gln Met Val His
                405             410             415

Gly Arg Ile Asp Glu Thr Leu Arg Val Arg Ser Thr Val Asn Ala Leu
            420             425             430

His Val Leu Val Asp Gln Gly Tyr Val Gly Arg Glu Asp Gly His Asn
            435             440             445

Leu Ile Glu Ser Tyr Glu Phe Leu Arg Leu Leu Glu His Arg Leu Gln
            450             455             460

Leu Glu Arg Ile Lys Arg Thr His Leu Leu Pro Lys Pro Asp Asp Arg
465             470             475             480

Met Asn Met Arg Trp Leu Ala Arg Ala Ser Gly Phe Thr Gly Ser Met
            485             490             495

Glu Gln Ser Ser Ala Lys Ala Met Glu Arg His Leu Arg Lys Val Arg
            500             505             510
```

UNITED STATES PATENT AND TRADEMARK OFFICE
CERTIFICATE OF CORRECTION

PATENT NO. : 7,262,035 B2
APPLICATION NO. : 10/062458
DATED : August 28, 2007
INVENTOR(S) : Jun Nakamura et al.

It is certified that error appears in the above-identified patent and that said Letters Patent is hereby corrected as shown below:

```
Leu Gln Ile Gln Ser Leu His Ser Gln Leu Phe Tyr Arg Pro Leu Leu
        515             520             525

Asn Ser Val Val Asn Leu Ser Ala Asp Ala Ile Arg Leu Ser Pro Asp
        530             535             540

Ala Ala Lys Leu Gln Leu Gly Ala Leu Gly Tyr Leu His Pro Ser Arg
545             550             555             560

Ala Tyr Glu His Leu Thr Ala Leu Ala Ser Gly Ala Ser Arg Lys Ala
            565             570             575

Lys Ile Gln Ala Met Leu Leu Pro Thr Leu Met Glu Trp Leu Ser Gln
            580             585             590

Thr Ala Glu Pro Asp Ala Gly Leu Leu Asn Tyr Arg Lys Leu Ser Asp
            595             600             605

Ala Ser Tyr Asp Arg Ser Trp Phe Leu Arg Met Leu Arg Asp Glu Gly
        610             615             620

Val Val Gly Gln Arg Leu Met Arg Ile Leu Gly Asn Ser Pro Tyr Ile
625             630             635             640

Ser Glu Leu Ile Ile Ser Thr Pro Asp Phe Val Lys Gln Leu Gly Asp
            645             650             655

Ala Ala Ser Gly Pro Lys Leu Leu Ala Thr Ala Pro Thr Gln Val Val
            660             665             670

Lys Ala Ile Lys Ala Thr Val Ser Arg His Glu Ser Pro Asp Arg Ala
            675             680             685
```

UNITED STATES PATENT AND TRADEMARK OFFICE
CERTIFICATE OF CORRECTION

| | |
|---|---|
| PATENT NO. | : 7,262,035 B2 |
| APPLICATION NO. | : 10/062458 |
| DATED | : August 28, 2007 |
| INVENTOR(S) | : Jun Nakamura et al. |

It is certified that error appears in the above-identified patent and that said Letters Patent is hereby corrected as shown below:

```
Ile Gln Ala Ala Arg Ser Leu Arg Arg Gln Glu Leu Ala Arg Ile Ala
    690             695             700

Ser Ala Asp Leu Leu Asn Met Leu Thr Val Gln Glu Val Cys Gln Ser
705             710             715             720

Leu Ser Leu Val Trp Asp Ala Val Leu Asp Ala Ala Leu Asp Ala Glu
            725             730             735

Ile Arg Ala Ala Leu Asn Asp Pro Gln Lys Pro Asp Gln Pro Leu Ala
        740             745             750

Asn Ile Ser Val Ile Gly Met Gly Arg Leu Gly Gly Ala Glu Leu Gly
        755             760             765

Tyr Gly Ser Asp Ala Asp Val Met Phe Val Cys Glu Pro Val Ala Gly
        770             775             780

Val Glu Glu His Glu Ala Val Thr Trp Ser Ile Ala Ile Cys Asp Ser
785             790             795             800

Met Arg Ser Arg Leu Ala Gln Pro Ser Gly Asp Pro Pro Leu Glu Val
            805             810             815

Asp Leu Gly Leu Arg Pro Glu Gly Arg Ser Gly Ala Ile Val Arg Thr
            820             825             830

Val Asp Ser Tyr Val Lys Tyr Tyr Glu Lys Trp Gly Glu Thr Trp Glu
            835             840             845

Ile Gln Ala Leu Leu Arg Ala Ala Trp Val Ala Gly Asp Arg Glu Leu
    850             855             860
```

UNITED STATES PATENT AND TRADEMARK OFFICE
CERTIFICATE OF CORRECTION

PATENT NO.        : 7,262,035 B2
APPLICATION NO.   : 10/062458
DATED             : August 28, 2007
INVENTOR(S)       : Jun Nakamura et al.

It is certified that error appears in the above-identified patent and that said Letters Patent is hereby corrected as shown below:

```
Gly Ile Lys Phe Leu Glu Ser Ile Asp Arg Phe Arg Tyr Pro Val Asp
865             870             875             880

Gly Ala Thr Gln Ala Gln Leu Arg Glu Val Arg Arg Ile Lys Ala Arg
            885             890             895

Val Asp Asn Glu Arg Leu Pro Arg Gly Ala Asp Arg Asn Thr His Thr
            900             905             910

Lys Leu Gly Arg Gly Ala Leu Thr Asp Ile Glu Trp Thr Val Gln Leu
            915             920             925

Leu Thr Met Met His Ala His Glu Ile Pro Glu Leu His Asn Thr Ser
        930             935             940

Thr Leu Glu Val Leu Glu Val Leu Glu Lys His Gln Ile Ile Asn Pro
945             950             955             960

Val Gln Val Gln Thr Leu Arg Glu Ala Trp Leu Thr Ala Thr Ala Ala
                965             970             975

Arg Asn Ala Leu Val Leu Val Arg Gly Lys Arg Leu Asp Gln Leu Pro
            980             985             990

Thr Pro Gly Pro His Leu Ala Gln  Val Ala Gly Ala Ser  Gly Trp Asp
            995             1000            1005

Pro Asn  Glu Tyr Gln Glu Tyr  Leu Glu Asn Tyr Leu  Lys Val Thr
    1010            1015             1020
```

UNITED STATES PATENT AND TRADEMARK OFFICE
CERTIFICATE OF CORRECTION

PATENT NO.         : 7,262,035 B2
APPLICATION NO.    : 10/062458
DATED              : August 28, 2007
INVENTOR(S)        : Jun Nakamura et al.

It is certified that error appears in the above-identified patent and that said Letters Patent is hereby corrected as shown below:

```
Arg Lys  Ser Arg Gln Val Val  Asp Glu Val Phe Trp  Gly Val Asp
    1025                 1030                 1035

Ser Met  Glu Gln Arg Glu Phe
    1040                 1045

<210>  4
<211>  29
<212>  DNA
<213>  Artificial Sequence

<220>
<223>  Description of Artificial Sequence: primer

<400>  4
ggggtcgacg gatcgacagg taatgcatt                                                29

<210>  5
<211>  29
<212>  DNA
<213>  Artificial Sequence

<220>
<223>  Description of Artificial Sequence: primer

<400>  5
ggggtcgacg gatccaccat gatggagga                                                29

<210>  6
<211>  22
<212>  DNA
<213>  Artificial Sequence

<220>
<223>  Description of Artificial Sequence: primer

<400>  6
cttcccagta gcaccatacg ac                                                       22

<210>  7
<211>  26
```

UNITED STATES PATENT AND TRADEMARK OFFICE
CERTIFICATE OF CORRECTION

PATENT NO.       : 7,262,035 B2
APPLICATION NO.  : 10/062458
DATED            : August 28, 2007
INVENTOR(S)      : Jun Nakamura et al.

It is certified that error appears in the above-identified patent and that said Letters Patent is hereby corrected as shown below:

```
<212>  DNA
<213>  Artificial Sequence

<220>
<223>  Description of Artificial Sequence: primer

<400>  7
ctggtggcag ttcgaagagg tccttg                                    26

<210>  8
<211>  26
<212>  DNA
<213>  Artificial Sequence

<220>
<223>  Description of Artificial Sequence: primer

<400>  8
ggacaaggac ctcttcgaac tgccag                                    26

<210>  9
<211>  26
<212>  DNA
<213>  Artificial Sequence

<220>
<223>  Description of Artificial Sequence: primer

<400>  9
cggcgagacc gtcgattggg aggagc                                    26

<210>  10
<211>  22
<212>  DNA
<213>  Artificial Sequence

<220>
<223>  Description of Artificial Sequence: primer

<400>  10
gtagcacctt acgaccaaac cg                                        22
```

UNITED STATES PATENT AND TRADEMARK OFFICE
CERTIFICATE OF CORRECTION

PATENT NO. : 7,262,035 B2
APPLICATION NO. : 10/062458
DATED : August 28, 2007
INVENTOR(S) : Jun Nakamura et al.

It is certified that error appears in the above-identified patent and that said Letters Patent is hereby corrected as shown below:

```
<210>  11
<211>  20
<212>  DNA
<213>  Artificial Sequence

<220>
<223>  Description of Artificial Sequence: primer

<400>  11
ggagccggtc gacgaggagc                                              20

<210>  12
<211>  25
<212>  DNA
<213>  Artificial Sequence

<220>
<223>  Description of Artificial Sequence: primer

<400>  12
gctagcctcg ggagctctct aggag                                        25

<210>  13
<211>  25
<212>  DNA
<213>  Artificial Sequence

<220>
<223>  Description of Artificial Sequence: primer

<400>  13
gatctttccc agactctggc cacgc                                        25

<210>  14
<211>  17
<212>  DNA
<213>  Artificial Sequence

<220>
<223>  Description of Artificial Sequence: primer
```

UNITED STATES PATENT AND TRADEMARK OFFICE
CERTIFICATE OF CORRECTION

PATENT NO. : 7,262,035 B2
APPLICATION NO. : 10/062458
DATED : August 28, 2007
INVENTOR(S) : Jun Nakamura et al.

It is certified that error appears in the above-identified patent and that said Letters Patent is hereby corrected as shown below:

```
<400>  14
cagttgtggc tgatccg                                                    17

<210>  15
<211>  18
<212>  DNA
<213>  Artificial Sequence

<220>
<223>  Description of Artificial Sequence: primer

<400>  15
ctttcccaga ctctggcc                                                   18

<210>  16
<211>  22
<212>  DNA
<213>  Artificial Sequence

<220>
<223>  Description of Artificial Sequence: primer

<400>  16
cgctgctata attgaacgtg ag                                              22

<210>  17
<211>  44
<212>  DNA
<213>  Artificial Sequence

<220>
<223>  Description of Artificial Sequence: primer

<400>  17
ctttgttgcc atatctgtgc gacgctgcta taattgaacg tgag                      44

<210>  18
<211>  21
<212>  DNA
<213>  Artificial Sequence
```

UNITED STATES PATENT AND TRADEMARK OFFICE
CERTIFICATE OF CORRECTION

PATENT NO. : 7,262,035 B2
APPLICATION NO. : 10/062458
DATED : August 28, 2007
INVENTOR(S) : Jun Nakamura et al.

It is certified that error appears in the above-identified patent and that said Letters Patent is hereby corrected as shown below:

```
<220>
<223>  Description of Artificial Sequence: primer

<400> 18
ccaccacgaa gtcggtggcg g                                              21

<210>  19
<211>  21
<212>  DNA
<213>  Artificial Sequence

<220>
<223>  Description of Artificial Sequence: primer

<400> 19
ttggagcctc gaagcctgga a                                              21

<210>  20
<211>  29
<212>  DNA
<213>  Brevibacterium flavum

<400> 20
tggtcatatc tgtgcgacgc tgccataat                                      29

<210>  21
<211>  29
<212>  DNA
<213>  Artificial Sequence

<220>
<223>  Description of Artificial Sequence: sequence of
       promoter

<400> 21
tggtcatatc tgtgcgacgc tgctataat                                      29

<210>  22
<211>  29
```

UNITED STATES PATENT AND TRADEMARK OFFICE
CERTIFICATE OF CORRECTION

PATENT NO. : 7,262,035 B2
APPLICATION NO. : 10/062458
DATED : August 28, 2007
INVENTOR(S) : Jun Nakamura et al.

It is certified that error appears in the above-identified patent and that said Letters Patent is hereby corrected as shown below:

```
<212>  DNA
<213>  Artificial Sequence

<220>
<223>  Description of Artificial Sequence: sequence of
       promoter

<400>  22
ttgccatatc tgtgcgacgc tgctataat                                      29

<210>  23
<211>  23
<212>  DNA
<213>  Artificial Sequence

<220>
<223>  Description of Artificial Sequence: primer

<400>  23
agacctacga gtccgccttt ttg                                            23

<210>  24
<211>  21
<212>  DNA
<213>  Artificial Sequence

<220>
<223>  Description of Artificial Sequence: primer

<400>  24
cgatcaccag caacccacgc a                                              21

<210>  25
<211>  477
<212>  PRT
<213>  Corynebacterium glutamicum

<400>  25

Met Ala Phe Glu Thr Pro Glu Glu Ile Val Lys Phe Ile Lys Asp Glu
1               5                   10                  15
```

UNITED STATES PATENT AND TRADEMARK OFFICE
CERTIFICATE OF CORRECTION

PATENT NO. : 7,262,035 B2
APPLICATION NO. : 10/062458
DATED : August 28, 2007
INVENTOR(S) : Jun Nakamura et al.

It is certified that error appears in the above-identified patent and that said Letters Patent is hereby corrected as shown below:

```
Asn Val Glu Phe Val Asp Val Arg Phe Thr Asp Leu Pro Gly Thr Glu
            20                  25                  30

Gln His Phe Ser Ile Pro Ala Ala Ser Phe Asp Ala Asp Thr Ile Glu
        35                  40                  45

Glu Gly Leu Ala Phe Asp Gly Ser Ser Ile Arg Gly Phe Thr Thr Ile
    50                  55                  60

Asp Glu Ser Asp Met Asn Leu Leu Pro Asp Leu Gly Thr Ala Thr Leu
65                  70                  75                  80

Asp Pro Phe Arg Lys Ala Lys Thr Leu Asn Val Lys Phe Phe Val His
            85                  90                  95

Asp Pro Phe Thr Arg Glu Ala Phe Ser Arg Asp Pro Arg Asn Val Ala
            100                 105                 110

Arg Lys Ala Glu Gln Tyr Leu Ala Ser Thr Gly Ile Ala Asp Thr Cys
        115                 120                 125

Asn Phe Gly Ala Glu Ala Glu Phe Tyr Leu Phe Asp Ser Val Arg Tyr
    130                 135                 140

Ser Thr Glu Met Asn Ser Gly Phe Tyr Glu Val Asp Thr Glu Glu Gly
145                 150                 155                 160

Trp Trp Asn Arg Gly Lys Glu Thr Asn Leu Asp Gly Thr Pro Asn Leu
            165                 170                 175
```

UNITED STATES PATENT AND TRADEMARK OFFICE
CERTIFICATE OF CORRECTION

PATENT NO. : 7,262,035 B2
APPLICATION NO. : 10/062458
DATED : August 28, 2007
INVENTOR(S) : Jun Nakamura et al.

It is certified that error appears in the above-identified patent and that said Letters Patent is hereby corrected as shown below:

```
Gly Ala Lys Asn Arg Val Lys Gly Gly Tyr Phe Pro Val Ala Pro Tyr
            180             185             190

Asp Gln Thr Val Asp Val Arg Asp Asp Met Val Arg Asn Leu Ala Ala
            195             200             205

Ser Gly Phe Ala Leu Glu Arg Phe His His Glu Val Gly Gly Gly Gln
    210             215             220

Gln Glu Ile Asn Tyr Arg Phe Asn Thr Met Leu His Ala Ala Asp Asp
225             230             235             240

Ile Gln Thr Phe Lys Tyr Ile Ile Lys Asn Thr Ala Arg Leu His Gly
            245             250             255

Lys Ala Ala Thr Phe Met Pro Lys Pro Leu Ala Gly Asp Asn Gly Ser
            260             265             270

Gly Met His Ala His Gln Ser Leu Trp Lys Asp Gly Lys Pro Leu Phe
            275             280             285

His Asp Glu Ser Gly Tyr Ala Gly Leu Ser Asp Ile Ala Arg Tyr Tyr
    290             295             300

Ile Gly Gly Ile Leu His His Ala Gly Ala Val Leu Ala Phe Thr Asn
305             310             315             320
```

UNITED STATES PATENT AND TRADEMARK OFFICE
CERTIFICATE OF CORRECTION

PATENT NO.      : 7,262,035 B2
APPLICATION NO. : 10/062458
DATED           : August 28, 2007
INVENTOR(S)     : Jun Nakamura et al.

It is certified that error appears in the above-identified patent and that said Letters Patent is hereby corrected as shown below:

```
Ala Thr Leu Asn Ser Tyr His Arg Leu Val Pro Gly Phe Glu Ala Pro
                325             330             335

Ile Asn Leu Val Tyr Ser Gln Arg Asn Arg Ser Ala Ala Val Arg Ile
            340             345             350

Pro Ile Thr Gly Ser Asn Pro Lys Ala Lys Arg Ile Glu Phe Arg Ala
        355             360             365

Pro Asp Pro Ser Gly Asn Pro Tyr Leu Gly Phe Ala Ala Met Met Met
    370             375             380

Ala Gly Leu Asp Gly Ile Lys Asn Arg Ile Glu Pro His Ala Pro Val
385             390             395             400

Asp Lys Asp Leu Tyr Glu Leu Pro Pro Glu Glu Ala Ala Ser Ile Pro
            405             410             415

Gln Ala Pro Thr Ser Leu Glu Ala Ser Leu Lys Ala Leu Gln Glu Asp
            420             425             430

Thr Asp Phe Leu Thr Glu Ser Asp Val Phe Thr Glu Asp Leu Ile Glu
        435             440             445

Ala Tyr Ile Gln Tyr Lys Tyr Asp Asn Glu Ile Ser Pro Val Arg Leu
    450             455             460

Arg Pro Thr Pro Gln Glu Phe Glu Leu Tyr Phe Asp Cys
465             470             475
```

Signed and Sealed this

Second Day of December, 2008

JON W. DUDAS
*Director of the United States Patent and Trademark Office*

UNITED STATES PATENT AND TRADEMARK OFFICE
CERTIFICATE OF CORRECTION

PATENT NO. : 7,262,035 B2 Page 1 of 1
APPLICATION NO. : 10/062458
DATED : August 28, 2007
INVENTOR(S) : Jun Nakamura et al.

It is certified that error appears in the above-identified patent and that said Letters Patent is hereby corrected as shown below:

Column 47, Claim 1, lines 10-11, should read,
-- activity is enhanced compared to an unmodified
coryneform bacterium, said modification comprising --.

Signed and Sealed this

Twenty-first Day of July, 2009

JOHN DOLL
*Acting Director of the United States Patent and Trademark Office*